(12) United States Patent
Kulp et al.

(10) Patent No.: US 8,163,874 B2
(45) Date of Patent: Apr. 24, 2012

(54) BETA HELICAL PEPTIDE STRUCTURES STABLE IN AQUEOUS AND NON-AQUEOUS MEDIA AND METHODS FOR PREPARING SAME

(75) Inventors: John L Kulp, Alexandria, VA (US); Thomas D Clark, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 802 days.

(21) Appl. No.: 12/187,308

(22) Filed: Aug. 6, 2008

(65) Prior Publication Data

US 2009/0076244 A1    Mar. 19, 2009

Related U.S. Application Data

(60) Provisional application No. 60/954,086, filed on Aug. 6, 2007.

(51) Int. Cl.
C07K 1/00 (2006.01)
(52) U.S. Cl. ........ 530/333; 530/338; 530/339; 530/326; 514/21.3; 514/21.4
(58) Field of Classification Search .................. None
See application file for complete search history.

(56) References Cited

U.S. PATENT DOCUMENTS

| | | | |
|---|---|---|---|
| 5,585,353 | A | 12/1996 | Merrifield et al. |
| 5,858,670 | A | 1/1999 | Lam et al. |
| 6,492,492 | B1 | 12/2002 | Stayton |
| 6,914,123 | B2 | 7/2005 | Cochran et al. |
| 7,176,276 | B2 | 2/2007 | Kourai et al. |
| 7,202,332 | B2 | 4/2007 | Arora et al. |
| 2002/0016010 | A1 | 2/2002 | Verdine et al. |
| 2003/0170826 | A1 | 9/2003 | Rabinovich et al. |
| 2004/0214272 | A1 | 10/2004 | La Rosa et al. |
| 2005/0164950 | A1 | 7/2005 | Fogelman et al. |
| 2005/0196754 | A1 | 9/2005 | Drmanac et al. |
| 2006/0147371 | A1 | 7/2006 | Tuszynski et al. |
| 2006/0149035 | A1 | 7/2006 | Rudolph et al. |

FOREIGN PATENT DOCUMENTS

WO    WO 2006/097693 A1 * 9/2006

OTHER PUBLICATIONS

Sastry et al., "Cyclic Peptide Helices: a Hybrid b-Hairpin/b-Helical Supersecondary Structure", J. Am. Chem. Soc., 2006, vol. 128, p. 10650-1 and S1-S9.*
Borgia et al., "Chemical Synthesis of Proteins", TIBTECH, 2000, vol. 18, p. 243-251.*
Xiao et al., "Electrostatic versus Steric Effects in Peptidomimicry: Synthesis and Secondary Structure Analysis of Gramicidin S Analogues with (E)-Alkene Peptide Isosteres", J. Am. Chem. Soc., 2005, vol. 127, p. 5742-3.*
D.T. Bong et al., "Self-Assembling Organic Nanotubes", Angew. Chem. Int. Ed., 2001, vol. 40, p. 988-1011.*
F. Rossi et al., "Zn2+-Complexation by a beta-Petidic Helix and Hairpin Containing Beta3-hCys and Beta3-hHis Building Blocks: Evidence from CD Measurements", Helvetica Chimica Acta, 2003, vol. 86, p. 2653-2661.*
Blanco et al., "Formation and Stability of beta-Hairpin Strutures in Polypeptides", Cur. Op. Struct. Biol., 1992, vol. 8, p. 107-111.*
Shankaramma et al., "Insertion of Methylene Units into the Turn Segment of Designed beta-Hairpin Peptides", J. Am. Chem. Soc., 1999, vol. 121, pp. 5360-5363.*
Souers et al. (1999) JACS 121 1817-1825).
Wang et al. (2005) Angew. Chem. Int. Ed. 44, 6525-6529.
Martin et al. (1994) EMBO J 13:5303-5309.
Suat Kee et al. (2003) Current Pharm. Design 9, 1209-1224.
Lorenzi et al. (1982) JACS 104, 1728-1733.
Clark et al. (2006) JACS 128, 10650-10651.
Alexopoulos et al. (2004) Acta Cryst. D60, 1971-1980.
Rossi et al. Helvetica Chemica Acta (2003) 86, 2653-2661.
Kenner, et.al., J. Chem. Soc., Chem. Commun. 1971, 636.
Backes, et al., J. A. J. Org. Chem. 1999, 64, 2322.
Backes, et al., J. Am. Chem. Soc. 1996, 118, 3055.
Yang, et al., Tetrahedron Lett. 1999, 40, 8197.
de Visser, et al., J. Pept. Res. 2003, 61, 298.
Qin, et al., J. Comb. Chem. 2003, 5, 353.
Bu, et al, J. Org. Chem. 2004, 69, 2681.
Qin, et al., Chem. 2004, 6, 398.
Qin, et al., Tetrahedron Lett. 2004, 45, 217-220.
Bourel-Bonnet, et al., J. Med. Chem. 2005, 48, 1330.
Bollhagen, et al., J. Chromatogr., A 1995, 711, 181.
Lew, et al., Anal. Biochem. 1997, 251, 113.
Taneja, et al., J. Chromatogr. 1984, 317, 1.
Ingenito et al., Org. Lett. 2002, 4, 1187.
Schnölzer et al., Int. J. Pept. Protein Res. 1992, 40, 180.
Souers et al. (1999) Identification of a Potent Heterocyclic Ligand to Somatostatin Receptor Subtype 5 by the Synthesis and Screening of â-Turn Mimetic Libraries, JACS 121 1817-1825).
Wang et al. (2005) Enhanced Metabolic Stability and Protein-Binding Properties of Artificial a Helices Derived from a Hydrogen-Bond Surrogate: Application to Bcl-x, Angew. Chem. Int. Ed. 44, 6525-6529.
Martin et al. The affinity-selection of a minibody polypeptide inhibitor of human interleukin-6, (1994) EMBO J 13:5303-5309.
Suat Kee et al. Design of p-turn Based Therapeutic Agents, (2003) Current Pharm. Design 9, 1209-1224.
Lorenzi et al. Nature and Relative Stability of Monomeric and Dimeric Species of the D,L-Alternating Octapeptide BOc-(L-Val-D-Val)4-0Me in Cyclohexane or Chloroform Solution (1982) JACS 104, 1728-1733.
Clark et al. Cyclic Peptide Helices: A Hybrid â-Hairpin/â-Helical Supersecondary Structure (2006) JACS 128, 10650-10651.

(Continued)

Primary Examiner — Anish Gupta
Assistant Examiner — Li Lee
(74) Attorney, Agent, or Firm — Amy Ressing; Roy Roberts

(57) ABSTRACT

Disclosed is a method of making peptide structures that are stable in aqueous and non-aqueous media where a first linear peptide chain comprising alternating D,L- or L,D-amino acids having an N and C termini is joined by at least one turn region to a second linear peptide chain comprising alternating D,L- or L,D-amino acids having an N and C termini. The peptide chains can be joined at the C terminus of one of the linear peptide chains with an N terminus of the other linear peptide chain, a C terminus of one of the linear peptide chains with a C terminus of the other linear peptide chain, or an N terminus of one of the linear peptide chains with an N terminus of the other linear peptide chain.

7 Claims, 12 Drawing Sheets

OTHER PUBLICATIONS

Alexopoulos et al. Solution and structure of an alternating D,L-peptide(2004) Acta Cryst. D60, 1971-1980.

Rossi et al. Zn2‡-Complexation by a b-Peptidic Helix and Hairpin Containing b3hCys and b3hHis Building Blocks: Evidence from CD Measurements, Helvetica Chemica Acta (2003) 86, 2653-2661.

Kenner, et.al., The Safety Catch Principle in Solid Phase Peptide Synthesis, J. Chem. Soc., Chem. Commun. 1971, 636.

Backes, et al., An Alkanesulfonamide "Safety-Catch" Linker for Solid-Phase Synthesis, J. A. J. Org. Chem. 1999, 64, 2322.

Backes, et al., Activation Method to Prepare a Highly Reactive Acylsulfonamide Safety-Catch Linker for Solid-Phase Synthesis, J. Am. Chem. Soc. 1996, 118, 3055.

Yang, et al., Solid phase synthesis of 'head-to-tail' cyclic peptides using a sulfonamide 'safety-catch' linker: the cleavage by cyclization approach, Tetrahedron Lett. 1999, 40, 8197.

de Visser, et al., Solid-phase synthesis of polymyxin B1 and analogues via a safety-catch approach, J. Pept. Res. 2003, 61, 298.

Qin, et al., A Chemical Approach to Generate Molecular Diversity Based on the Scaffold of Cyclic Decapeptide Antibiotic Tyrocidine AJ. Comb. Chem. 2003, 5, 353.

Bu, et al, Synthesis of Gramacidin S and it's Analogues via an On-Resin Macrolamatization Assisted by a Predisposed Conformation or the Linear Precursors, J. Org. Chem. 2004, 69, 2681.

Qin, et al., Optimization of Antibacterial Cyclic Decapeptides, Chem. 2004, 6, 398.

Qin, et al., Facile solid-phase synthesis of cyclic decapeptide antibiotic streptocidins A±D, Tetrahedron Lett. 2004, 45, 217-220.

Bourel-Bonnet, et al., Solid-Phase Total Synthesis of Kahalalide A and Related Analogues, J. Med. Chem. 2005, 48, 1330.

Bollhagen, et al., High-performance liquid chromatographic purification of extremely hydrophobic peptides: transmembrane segments, J. Chromatogr., A 1995, 711, 181.

Lew, et al., Simple Procedure for Reversed-Phase High Performance Liquid Chromatographic Purification of Long Hydrophobic Peptides That Form Transmembrane HelicesAnal. Biochem, 1975, 251, 113.

Taneja, et al., Separation of Hydrophobic Peptide Polymers by Size Exclusion and Reversed-Phase High-Performance Liquid Chromatography, J. Chromatogr. 1984, 317, 1.

Ingenito et al., Efficient Loading of Sulfonamide Safety-Catch Linkers by Fmoc Amino Acid FluoridesOrg. Lett. 2002, 4, 1187.

Schnölzer et al., In situ neutralization in Boc-chemistry solid phase peptide synthesis Rapid, high yield assembly of difficult sequences, Int. J. Pept. Protein Res. 1992, 40, 180.

* cited by examiner

SEQ. ID. NO. 1

SEQ. ID. NO. 3

SEQ. ID. NO 2

SEQUENCE LISTING

```
<160> NUMBER OF SEQ ID NOS: 7

<210> SEQ ID NO 1
<211> LENGTH: 22
<212> TYPE: PRT
<213> ORGANISM: Artificial
<220> FEATURE:
<223> OTHER INFORMATION: artificial sequence, synthesized
<220> FEATURE:
<221> NAME/KEY: MISC_FEATURE
<222> LOCATION: (1)..(21)
<223> OTHER INFORMATION: Alternating D- L- amino acids: D-Leu, L-Glu,
      D-Val, L-Arg, D-Leu, L-Thr, D-Ala, L-Thr, D-Val, L-Pro, D-Ala,
      L-Glu, D-Leu, L-Lys, D-Val, L-Thr, D-Leu, L-Thr, D-Ala, L-Pro,
      Gly

<400> SEQUENCE: 1

Leu Glu Val Arg Leu Thr Ala Thr Val Val Pro Ala Glu Leu Lys Val
1               5                   10                  15

Thr Leu Thr Ala Pro Gly
            20

<210> SEQ ID NO 2
<211> LENGTH: 29
<212> TYPE: PRT
<213> ORGANISM: Artificial
<220> FEATURE:
<223> OTHER INFORMATION: Artificial sequence, synthesized
<220> FEATURE:
<221> NAME/KEY: MISC_FEATURE
<222> LOCATION: (1)..(28)
<223> OTHER INFORMATION: Alternating D- L- amino acids  D-Trp L-Glu
      D-Val L-Tyr D-Leu L-Gln D-Ala L-Lys L-Leu L-Thr D -Val L-Ser D-Trp
      D-Orn D-Ala L-Glu D-Leu L-Tyr D-Leu L-Ser D-Ala L-Arg D-Val L-Thr
      D-Val L-Gln D-Ala L-Pro Gly
<220> FEATURE:
<221> NAME/KEY: MOD_RES
<222> LOCATION: (14)..(14)
<223> OTHER INFORMATION: Xaa is Orn

<400> SEQUENCE: 2

Trp Glu Val Tyr Leu Gln Ala Lys Leu Thr Val Ser Trp Xaa Ala Glu
1               5                   10                  15

Leu Tyr Leu Ser Ala Arg Val Thr Val Gln Ala Pro Gly
            20                  25

<210> SEQ ID NO 3
<211> LENGTH: 22
<212> TYPE: PRT
<213> ORGANISM: Artificial
<220> FEATURE:
<223> OTHER INFORMATION: artificial sequence, synthesized
```

```
<220> FEATURE:
<221> NAME/KEY: MISC_FEATURE
<222> LOCATION: (1)..(2)
<223> OTHER INFORMATION: Alternating D- L- amino acids  L-Val D-Pro Gly
      L-Val D-Val L-Val D-Val L-Val D-Val L-Val D-Val L-Val D-Pro Gly
      L-Val D-Val L-Val D-Val L-Val D-Val L-Val D-Val
<220> FEATURE:
<221> NAME/KEY: MISC_FEATURE
<222> LOCATION: (4)..(13)
<223> OTHER INFORMATION: Alternating D- L- amino acids  L-Val D-Pro Gly
      L-Val D-Val L-Val D-Val L-Val D-Val L-Val D-Val L-Val D-Pro Gly
      L-Val D-Val L-Val D-Val L-Val D-Val L-Val D-Val
<220> FEATURE:
<221> NAME/KEY: MISC_FEATURE
<222> LOCATION: (15)..(22)
<223> OTHER INFORMATION: Alternating D- L- amino acids  L-Val D-Pro Gly
      L-Val D-Val L-Val D-Val L-Val D-Val L-Val D-Val L-Val D-Pro Gly
      L-Val D-Val L-Val D-Val L-Val D-Val L-Val D-Val

<400> SEQUENCE: 3

Val Pro Gly Val Val Val Val Val Val Val Val Pro Gly Val Val
1               5                   10                  15

Val Val Val Val Val Val
            20

<210> SEQ ID NO 4
<211> LENGTH: 22
<212> TYPE: PRT
<213> ORGANISM: Artificial
<220> FEATURE:
<223> OTHER INFORMATION: artificial sequence, synthesized
<220> FEATURE:
<221> NAME/KEY: MISC_FEATURE
<222> LOCATION: (1)..(13)
<223> OTHER INFORMATION: Alternating D-, L- amino acids  D-Leu L-Pro Gly
      D-Leu L-Leu D-Leu L-Leu D-Leu L-Leu D-Leu L-Leu D-Leu L-Pro Gly D
      Leu L-Leu D-Leu L-Leu D-Leu L-Leu D-Leu L-Leu
<220> FEATURE:
<221> NAME/KEY: MISC_FEATURE
<222> LOCATION: (15)..(22)
<223> OTHER INFORMATION: Alternating D-, L- amino acids  D-Leu L-Pro Gly
      D-Leu L-Leu D-Leu L-Leu D-Leu L-Leu D-Leu L-Leu D-Leu L-Pro Gly D
      Leu L-Leu D-Leu L-Leu D-Leu L-Leu D-Leu L-Leu

<400> SEQUENCE: 4

Leu Pro Gly Leu Leu Leu Leu Leu Leu Leu Leu Pro Gly Leu Leu
1               5                   10                  15

Leu Leu Leu Leu Leu Leu
            20

<210> SEQ ID NO 5
<211> LENGTH: 16
<212> TYPE: PRT
<213> ORGANISM: Artificial
<220> FEATURE:
<223> OTHER INFORMATION: artificial sequence, synthesized
<220> FEATURE:
<221> NAME/KEY: MISC_FEATURE
<222> LOCATION: (1)..(10)
<223> OTHER INFORMATION: Alternating D- L- amino acids  D-Val L-Val,
      D-Val, L-Val, D-Val, L-Val, D-Val, L-Val, D-Val, L-Pro, Gly,
      D-Val, L-Val, D-Val, L-Val, D-Val
<220> FEATURE:
<221> NAME/KEY: MISC_FEATURE
<222> LOCATION: (12)..(16)
<223> OTHER INFORMATION: Alternating D- L- amino acids  D-Val L-Val,
      D-Val, L-Val, D-Val, L-Val, D-Val, L-Val, D-Val, L-Pro, Gly,
      D-Val, L-Val, D-Val, L-Val, D-Val

<400> SEQUENCE: 5

Val Val Val Val Val Val Val Val Val Pro Gly Val Val Val Val Val
1               5                   10                  15
```

```
<210> SEQ ID NO 6
<211> LENGTH: 22
<212> TYPE: PRT
<213> ORGANISM: Artificial
<220> FEATURE:
<223> OTHER INFORMATION: artificial sequence, synthesized
<220> FEATURE:
<221> NAME/KEY: MISC_FEATURE
<222> LOCATION: (1)..(2)
<223> OTHER INFORMATION: Alternating D- L- sequences  L-Val D-Pro Gly
     L-Val D-Val L-Val D-Val L-Val D-Val L-Val D-Val L-Val D-Pro Gly
     L-Val D-Val L-Val D-Val L-Val D-Val L-Val D-Val
<220> FEATURE:
<221> NAME/KEY: MISC_FEATURE
<222> LOCATION: (4)..(13)
<223> OTHER INFORMATION: Alternating D- L- sequences  L-Val D-Pro Gly
     L-Val D-Val L-Val D-Val L-Val D-Val L-Val D-Val L-Val D-Pro Gly
     L-Val D-Val L-Val D-Val L-Val D-Val L-Val D-Val
<220> FEATURE:
<221> NAME/KEY: MISC_FEATURE
<222> LOCATION: (15)..(22)
<223> OTHER INFORMATION: Alternating D- L- sequences  L-Val D-Pro Gly
     L-Val D-Val L-Val D-Val L-Val D-Val L-Val D-Val L-Val D-Pro Gly
     L-Val D-Val L-Val D-Val L-Val D-Val L-Val D-Val

<400> SEQUENCE: 6

Val Pro Gly Val Val Val Val Val Val Val Val Pro Gly Val Val
1               5                   10                  15

Val Val Val Val Val Val
            20

<210> SEQ ID NO 7
<211> LENGTH: 22
<212> TYPE: PRT
<213> ORGANISM: Artificial
<220> FEATURE:
<223> OTHER INFORMATION: artificial sequence, synthesized
<220> FEATURE:
<221> NAME/KEY: MISC_FEATURE
<222> LOCATION: (1)..(2)
<223> OTHER INFORMATION: Alternating D- L- amino acids D-Leu L-Pro Gly
     D-Leu L-Leu D-Leu L-Leu D-Leu L-Leu D-Leu L-Leu D-Leu L-Pro Gly D
     Leu L-Leu D-Leu L-Leu D-Leu L-Leu D-Leu L-Leu
<220> FEATURE:
<221> NAME/KEY: MISC_FEATURE
<222> LOCATION: (4)..(13)
<223> OTHER INFORMATION: Alternating D- L- amino acids D-Leu L-Pro Gly
     D-Leu L-Leu D-Leu L-Leu D-Leu L-Leu D-Leu L-Leu D-Leu L-Pro Gly D
     Leu L-Leu D-Leu L-Leu D-Leu L-Leu D-Leu L-Leu
<220> FEATURE:
<221> NAME/KEY: MISC_FEATURE
<222> LOCATION: (15)..(22)
<223> OTHER INFORMATION: Alternating D- L- amino acids D-Leu L-Pro Gly
     D-Leu L-Leu D-Leu L-Leu D-Leu L-Leu D-Leu L-Leu D-Leu L-Pro Gly D
     Leu L-Leu D-Leu L-Leu D-Leu L-Leu D-Leu L-Leu

<400> SEQUENCE: 7

Leu Pro Gly Leu Leu Leu Leu Leu Leu Leu Leu Leu Pro Gly Leu Leu
1               5                   10                  15

Leu Leu Leu Leu Leu Leu
            20
```

US 8,163,874 B2

BETA HELICAL PEPTIDE STRUCTURES STABLE IN AQUEOUS AND NON-AQUEOUS MEDIA AND METHODS FOR PREPARING SAME

CROSS-REFERENCE TO RELATED APPLICATIONS

This application is a Non-Prov of Prov (35 USC 119(e)) application 60/954,086 filed on Aug. 6, 2007, which is incorporated in full herein by reference.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

In an aqueous environment, peptides and proteins fold into conformationally limited structures that have the ability to interact with other molecular species and initiate biological responses. These interactions can be defined as, but are not limited to, protein-protein, ligand-receptor, substrate-enzyme, antigen-antibody and protein-nucleic acid recognition. Disruption or enhancement of these macromolecular interactions often cannot be accomplished with small molecules. Using larger molecules to disrupt or enhance biological interactions requires the mimicking of the protein's native spatial configuration. Using a large molecule that has a close spatial homology to the native protein ensures high affinity targeting of the desired species. Compounds that can specifically disrupt or enhance these macromolecular interactions would be invaluable tools in bionanotechnology, and, potentially, as lead compounds for the development of new drugs.

The conformation of a protein is defined by secondary structural elements, which include beta-sheets, beta-turns, alpha-helices, $3_{10}$-helices, pi-helices, and loops. These secondary structures participate broadly in moderating biological processes including specific recognition of macromolecular interactions. Exposed secondary structural elements on the surfaces of proteins are often important for the specific recognition of other biomolecules. Short peptides, having less then 20 amino acids, corresponding to the secondary structural region in a protein do not remain in the same secondary structure once the peptide is excised from the protein. Short peptides, of less then 20 amino acids, that can adopt secondary structural elements are expected to be useful models for the predictable design of bioactive molecules.

Many peptides are highly flexible and do not fold into unique conformations; thus these peptides cannot maintain the structure that they adopt when they are part of a full-length protein. This flexibility decreases the affinity of the peptide for a macromolecular target because some of the free energy of binding is squandered in paying the entropic cost of constraining the peptide into the proper conformation for binding. The conformational flexibility of peptides thus significantly compromises their potential use as drugs. Many techniques have been developed to constrain the peptides into singular conformations (hydrogen-bond surrogate, disulfide bridges, and other side chain cross linking methods). Constrained peptides having high binding affinities to macromolecular target have found wide use in analyzing structure-function relationships within macromolecular interactions.

Constrained peptide scaffolds, capable of presenting a sequence of interest as a conformationally-restricted body have been identified, including thioether-linked cyclic structures (Souers et al. (1999) JACS 121 1817-1825), hydrogen-bond surrogates (Wang et al. (2005) Angew. Chem. Int. Ed. 44, 6525-6529, U.S. Pat. No. 7,202,332), leucine-zipper motifs (Martin et al. (1994) EMBO J. 13:5303-5309), tryptophan-zipper scaffold that forms stable beta-hairpins in solution (U.S. Pat. No. 6,914,123) and many others. Beta turns are commonly involved in the molecular recognition process and are thus desirable for disrupting or enhancing binding (Smith & Pease (1980) CRC Crit. Rev Biochem 8:315-399). Currently, a commercial peptide drug, based on a beta-turn, has been approved by the FDA for clinical use: Octreotide (brand name Sandostatin®, Novartis Pharmaceuticals). Many of the identified beta-turn peptides are cyclopeptides that are synthesized by covalently attaching the N and C termini of the peptide (Suat Kee et al. (2003) Current Pharm. Design 9, 1209-1224). Many of these cyclic peptides still have a large degree of conformational heterogeneity and need to be further stabilized.

Peptides composed of hydrophobic, alternating D and L-amino acids (D,L-peptides) fold into beta helices in nonpolar environments. A given D,L-peptide usually forms a mixture of beta-helical species, including single-stranded, parallel double-stranded, and antiparallel double-stranded beta helices. One class of peptide sequences that display such conformational promiscuity is oligo D,L-valine peptides (Lorenzi et al. (1982) JACS 104, 1728-1733). To reduce the conformational heterogeneity of the beta-helices, Clark et al. developed a strategy for limiting the number of structural states available to the valine beta helix in nonpolar organic solvents (Clark et al. (2006) JACS 128, 10650-10651). We note that this disclosure was limited to the design of peptides that fold into the correct structures only in nonpolar organic solvents; however, many potential applications of constrained peptides—including the design of lead compounds for the development of new drugs—require that the peptide fold into the correct structure in aqueous media. Satisfying this requirement can be difficult because, in aqueous media, water competes for hydrogen bonding partners with the internal hydrogen bonds that stabilize the peptide's conformation, thus disrupting the peptide's structure. Thus, the design of beta-helical peptides that have well-defined and predictable structures in aqueous media would pave the way to a host of potential applications in biotechnology.

This beta-helical structure use as a scaffold for displaying libraries of peptide/peptidometric side chains as a way of disrupting or enhancing macromolecular interactions. Previously, nearly all beta-helical peptides examined were only soluble in organic solvents, and none of this work suggested that the correct conformation could be attained in aqueous media. Alexopoulos et al. (2004) Acta Cryst. D60, 1971-1980, reported a water-soluble D,L-peptide designed to fold into a beta-helical structure. Using x-ray crystallography, the authors showed that the peptide, an oligo D,L-tyrosine, forms a beta-helical dimer in the solid state. Only indirect evidence for the aggregation of the peptide in aqueous media was provided. The aggregation was not demonstrated to be due to the formation of a beta-helical dimer.

BRIEF SUMMARY OF THE INVENTION

For the use of the beta-helical peptide scaffold as a tool in bionanotechnology, a method to produce water-soluble beta-helices is presented. This disclosure describes a new method of constraining water-soluble, cyclic peptides composed of alternating D- and L-amino acid sequences that have the correct spatial homogeneity to form beta-turn, beta-sheet, and helical secondary structures. This invention is directed generally to methods of preparing these constrained peptides and peptidometics. This invention has implications not only for peptide and protein chemistry but also for the identification and optimization of constrained peptides for use as lead compounds for the development of new drugs. Furthermore, this invention will, in principle, allow the preparation of large numbers of different beta-helical peptides (libraries), either combinatorially or serially, which can then be screened for binding to biological targets.

Disclosed is a method of making peptide structures that are stable in aqueous and non-aqueous media where a first linear peptide chain comprising alternating D,L- or L,D-amino acids having an N and C termini is joined by at least one turn region to a second linear peptide chain comprising alternating D,L- or L,D-amino acids having an N and C termini. The peptide chains can be joined at the C terminus of one of the linear peptide chains with an N terminus of the other linear peptide chain, a C terminus of one of the linear peptide chains with a C terminus of the other linear peptide chain, or an N terminus of one of the linear peptide chains with an N terminus of the other linear peptide chain. The turn region includes, but is not limited to a peptide having an amino acid sequence with a length between 1 and 6 amino acid residues configured to form a turn region, such as L-Pro-Gly, D-Pro-Gly, $^\delta$Orn, Asn-Gly, Ava, D-$^\delta$Orn, or $^\epsilon$Lys. The turn region includes, but is not limited to, a sidechain-linked bridges wherein the linking bond is located between two carbon atoms, two heteroatoms, or a carbon and a heteroatom. The turn region includes, but is not limited to, a backbone linkage wherein the linking bond is an ester, an amide, or a heteroatom-based analogue of an ester or amide, and a backbone isostere linkage such as a thioester, a thioamide, a phosphoester, a sulfonyl ester, or a phosphoramide. The turn region includes, but is not limited to, a backbone isostere linkage comprising an alkene-based hydrocarbon linkage intended to mimic the tetrahedran intermediate of amide or ester hydrolysis. The first and second peptide chains of alternating D,L-amino acids may further comprise at least one achiral residue such as glycine. The first and second peptide chains of alternating D,L-amino acids may also further comprise all-L or all-D amino acids ranging from 2 to 5 amino acid residues.

DETAILED DESCRIPTION OF THE INVENTION

Disclosed is a structural scaffold for creating new abiotic peptides for the purpose of influencing biological processes. This new peptide scaffold shows a tolerance towards chemical diversity of the amino acid composition, allowing for, in principle, the preparation of large numbers of peptides (libraries) based on this scaffold. One embodiment provides for use of the peptide scaffold to display and stabilize a variety of secondary structures in aqueous solutions, including beta-hairpins, beta-sheets, and helical conformations. Stabilization of the backbone allows precise sidechain display, which will increase the affinity of the peptides for macromolecular targets and make this invention an invaluable tool in bionanotechnology. Methods of preparing and using such templates are presented, which can provide superiority in mimicking in vivo macromolecular interactions and thus designing novel abiotic therapeutic peptides/peptidometics. The peptide scaffold could be useful for studying biological processes and drug development.

Figure 1:
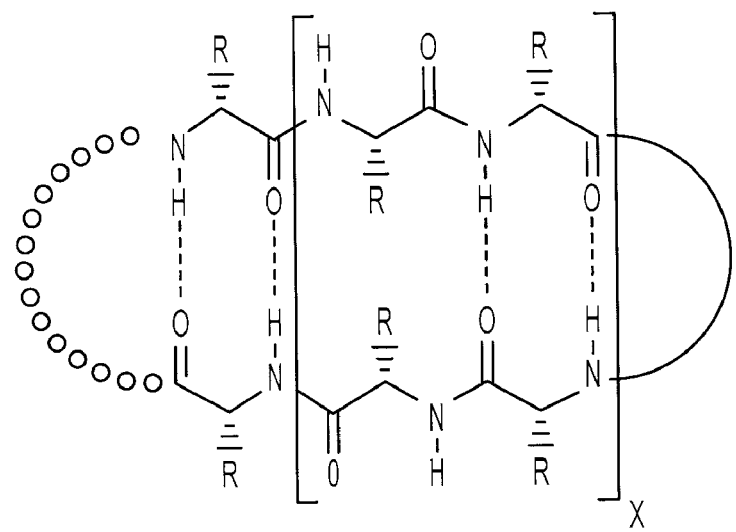
FIG. 1 shows a formula of alternating D,L-amino acids within cyclic peptide.
Figure 2:
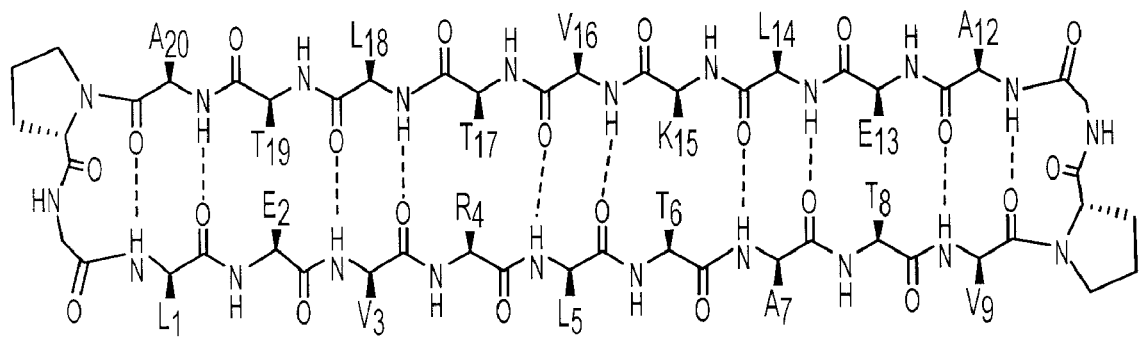
FIG. 2 shows the structure of peptide 1 (SEQ. ID No. 1)
Figure 3:
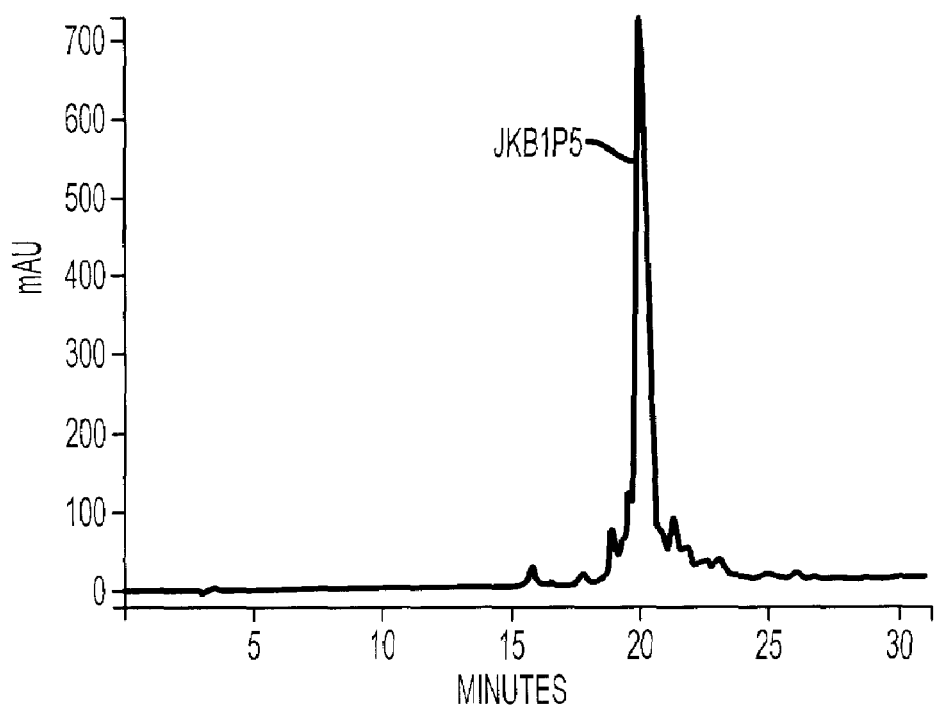
FIG. 3 shows the HPLC trace of crude product from peptide 1 synthesis.

FIG. 1 shows a compound of Formula I, which is the general outline of alternating D,L-amino acids within a cyclic peptide. The gray and black coloring represents the different chirality for the alternating D,L-sequences. The X signifies the number of repeats with a minimum of 3 for beta helical folding. The semicircles on the left and right denote the turn regions joining the two D,L-strands, albeit only 1 turn is necessary for beta helical stabilization. The synthesis of the linear peptide chain can be carried out via standard solid phase peptide synthesis. The N-terminal residue is transiently protected while the resin is activated for cleavage. The N-terminal is deprotected before cleavage. The peptide is cleaved from the resin by a process known as cleavage by cyclization. This process yields cyclic peptides containing the designed peptide sequence. FIG. 2 shows the structure of peptide 1 (SEQ. ID No. 1), where the gray residues are D-amino acids and black are L-amino acids, dotted lines are beta-sheet-like hydrogen bonding. FIG. 3 shows an HPLC trace of the crude product; the high purity of the crude material suggests that the cyclization reaction is self-selecting, since only peptides with the correct sequence and conformation will properly cyclize and cleave from the resin. This compound has alternating D,L-amino acids with a minimum of one of each kind of isomer. This alternating D,L-sequence predisposes the peptide to adopt a beta-helical secondary structure. Note that the alternating D,L-sequence may also contain achiral residues such as glycine or may contain short stretches of all-L or all-D amino acids ranging from 2 to 5 amino acid residues. The turn regions of the peptide prevent the two strands of the beta helix from coming apart and eliminate the conformational heterogeneity observed previously for linear D,L-peptides. These turn regions can be introduced by natural and normatural amino acids with a length between 1 and 6 amino acid residues configured to form a turn region including, but not limited to, L-Pro-Gly, D-Pro-Gly, $^\delta$Orn, Asn-Gly, Ava, D-$^\delta$Orn, $^\epsilon$Lys, and sidechain-linked-disulfide bridges. Additionally, the turn region can include, but is not limited to, a sidechain-linked bridges wherein the linking bond is located between two carbon atoms, two heteroatoms, or a carbon and a heteroatom. Further, the turn region also includes, but is not limited to, a backbone linkage wherein the linking bond is an ester, an amide, or a heteroatom-based analogue of an ester or amide, or a backbone isostere linkage such as a thioester, a thioamide, a phosphoester, a sulfonyl ester, or a phosphoramide, or a backbone isostere linkage comprising an alkene-based hydrocarbon linkage intended to mimic the tetrahedran intermediate of amide or ester hydrolysis. L-Pro-Gly, D-Pro-Gly, and $^\delta$Orn, have been shown to be compatible with the beta-hairpin/beta-helix motif. Any of the above methods should provide the correct structural element for the turn region of the beta-hairpin/beta-helix supersecondary structure.

Figure 4:
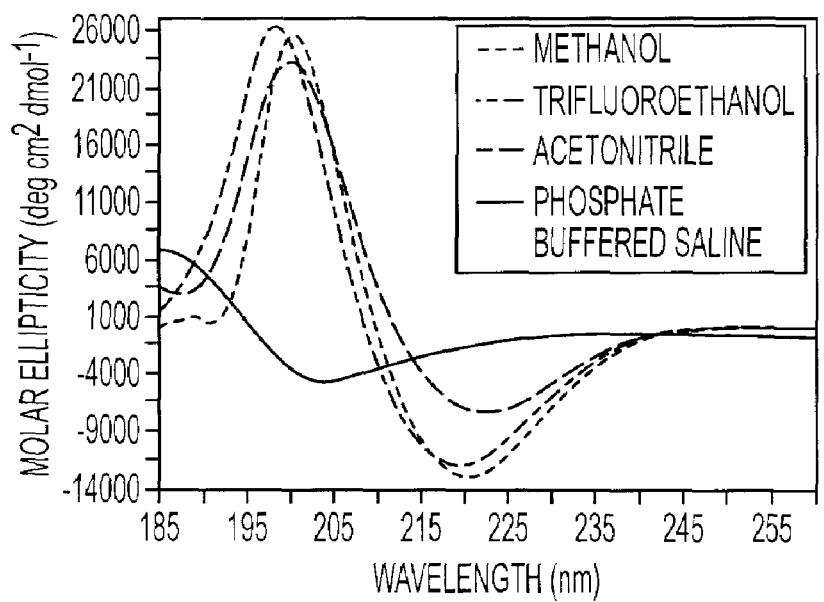
FIG. 4 shows the far UV-CD spectra of peptide 1 dissolved in various solvents.
Figure 5:
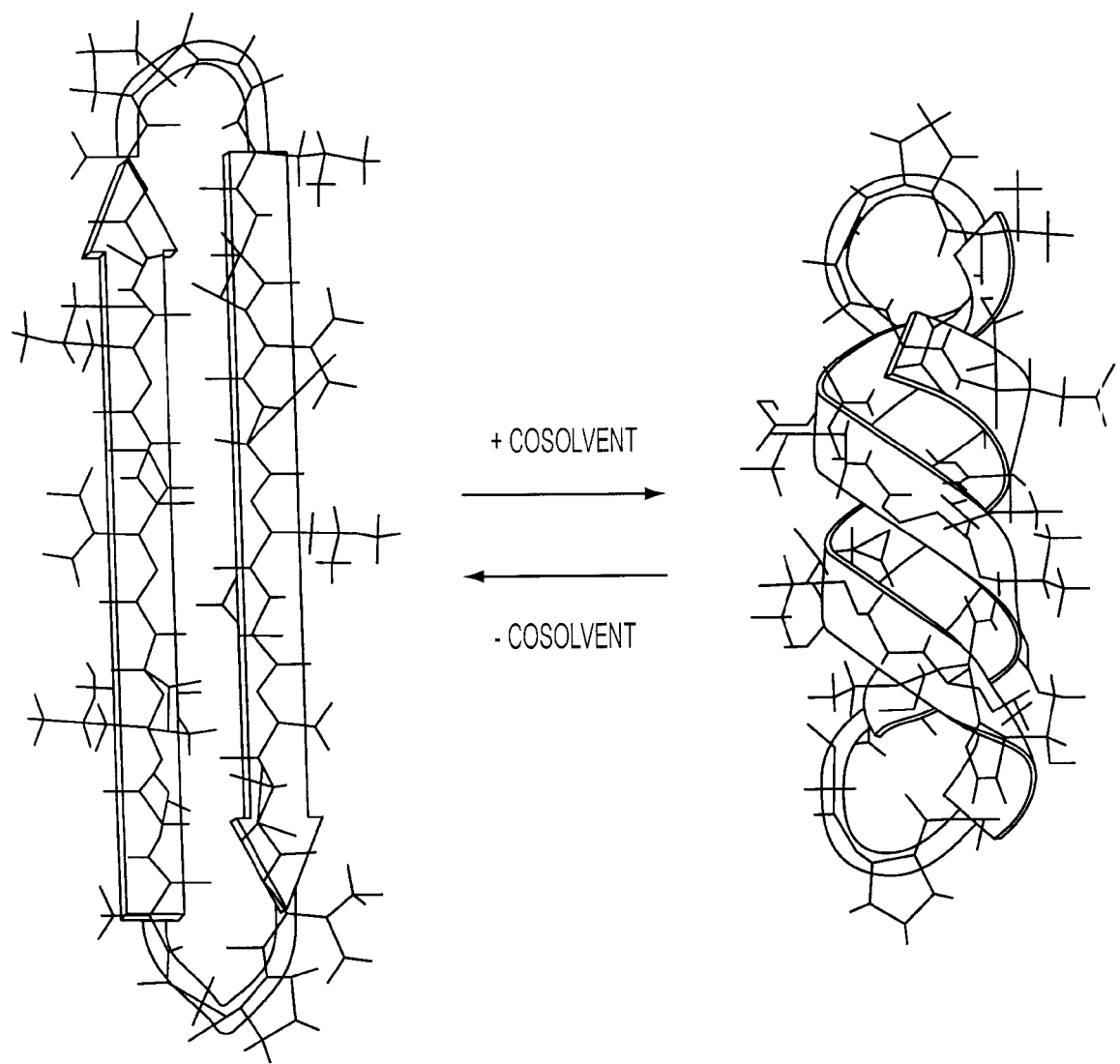
FIG. 5 shows the energy minimized models of the peptide 1 (SEQ. ID No. 1) in the two conformations.

The water solubility of these peptides/peptidometrics is defined by the correct choice of sidechain functionalities. Peptide 1 (SEQ ID No. 1) has a solubility of >10 mM in an aqueous medium as confirmed by NMR. The circular dichroism (CD) studies of peptide 1 show that in water, the peptide displays a beta-hairpin-type of secondary structure as noted by the negative band centered at 203 nm (FIG. 4) (Rossi et al. Helvetica Chemica Acta (2003) 86, 2653-2661). With the introduction of cosolvents, the peptide readily folds into the beta-hairpin/beta-helix conformation as seen by the negative band centered at 219 nm (FIG. 4). Additional CD data shows that this peptide has a large enough internal stability, through hydrogen bonding, to resist thermal denaturation. The beta-hairpin structure seen in the aqueous state (100 mM phosphate buffered saline buffer) does not change at temperatures ranging from about 5° C. to about 95° C., thus there is no unfolding to a more unstructured state. In both methanol and trifluoroethanol, the beta-helical CD spectra do not significantly change suggesting that the helical structure can resist thermal denaturation up to 85° C. FIG. 5 shows the energy minimized models of the peptide in the two conformations.

The uses of the peptide relate to a method for promoting cell death. This method involves mimicking the sequence of Bak BH3 protein by displaying the important amino acid side chains on our beta-hairpin/beta-helical scaffold. Another target will be the p53/hDM2 interaction, where hDM2 negatively regulates p53 tumor suppression activity. hDM2 stimulates p53 degradation and is over expressed in cancer cells. Others have demonstrated the disruption of this macromolecular interaction using alpha-helices, beta-sheets, and non-natural beta-amino acid peptides. Other targets where the peptide scaffold described here could be applied include, but are not limited to, Jun-Jun and/or Jun-Fos (cell death), smatostatin analogs (similar to Octreotide for treatment of severe diarrhea in patents with intestinal tumors), integrins (inhibition of platelet aggregation and subsequent thrombus formation), and many other targets that contain secondary structural elements at the interface of the macromolecular interaction.

The method described herein provides a procedure for preparing water-soluble, abiotic peptide motifs that are a hybrid of beta-hairpin and beta-helical supersecondary structures. This disclosure describes the preparation of the first-ever aqueous beta-hairpin/beta-helical peptide and the generality of the method for producing a library of peptides/peptidometics based on the predetermined backbone conformation, thus targeting a variety of macromolecular species. This method provides many advantages over other methods for preparing stabilized peptide structures:

Natural protease enzymes, which act on substrates composed of all-L amino acids, typically do not cleave at sites adjacent to D-amino acid residues. This observation suggests that the D,L-peptide scaffold disclosed herein will be resistant to protease degradation and would, therefore, have greater bioavailability with respect to peptides composed of all-L amino acids. Indeed, rapid digestion of peptide therapeutics by proteases has limited their usefulness as drugs. Efforts to experimentally demonstrate the resistance of our peptide scaffold to protease digestion are currently underway. D-amino acid antibiotic peptides are disclosed in U.S. Pat. No. 5,585,353. Patents of general sequence and/or method of producing any sequence, for instance, an alternating hydrophobic-hydrophilic amino acid sequence is disclosed in U.S. Pat. No. 7,176,276.

The peptide scaffold described in this disclosure contains beta-hairpin, beta-sheet, and helical segments, which individually have been used to disrupt macromolecular interactions. The disclosed peptide scaffold can, in principle, be used as a multivalent agent for binding to multiple macromolecular targets via a variety of displayed secondary structural elements. U.S. Pat. No. 6,914,123 discloses using a tryptophan zipper scaffold to stabilize the beta-hairpin conformation.

The disclosed method shows a lower conformational heterogeneity then other methods of stabilizing secondary structural elements. Having a discrete structural state implies higher affinity binding to a selected target. Higher affinity binding parallels high effectiveness and fewer side effects of the therapeutic peptide.

Figure 6A:
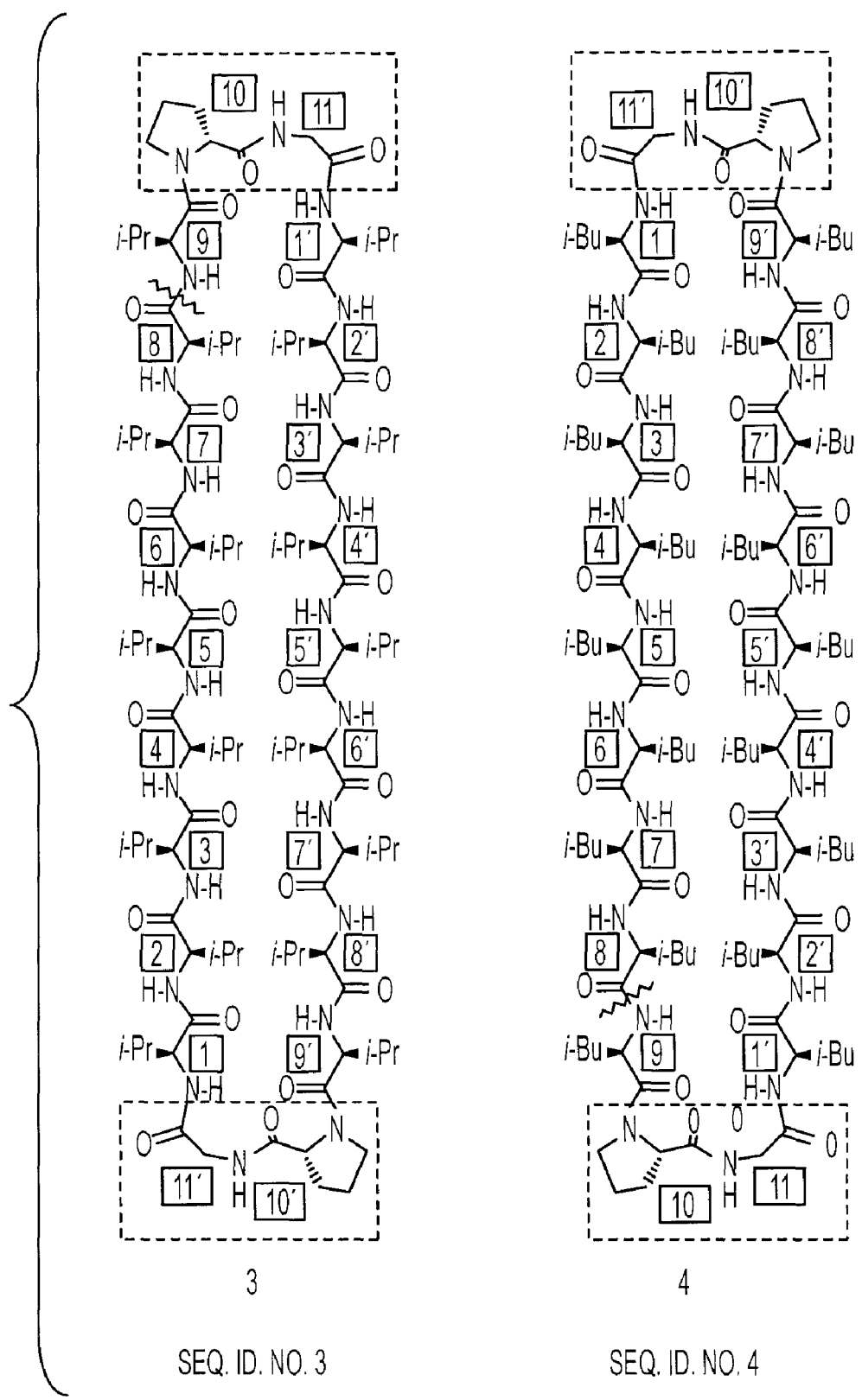
FIG. 6a shows the chemical structures of peptides 3 (SEQ. ID No. 3) and 4 (SEQ. ID No. 4)

FIG. 6A shows peptide 3 (SEQ. ID No. 3), Cyclo{[(L-Val-D-Val)$_4$-(L-Val-D-Pro-Gly)]$_2^-$} and peptide 4, (SEQ. ID No. 4), cyclo{[(D-Leu-L-Leu)$_4$-(D-Leu-L-Pro-Gly)]$_2^-$}, which were designed by joining two copies of the corresponding linear D,L-peptide with two copies of the reverse-turn sequences D-Pro-Gly and L-Pro-Gly, respectively. The linear precursors to peptide 3, lin3, (SEQ. ID No. 6) and peptide 4, lin-4 (SEQ. ID No. 7) were synthesized via stepwise solid-phase peptide synthesis (SPPS) using an alkanesulfonamide safety-catch linker (AS-SCL), originally developed by Kenner, et. al., J. Chem. Soc., Chem. Commun. 1971, 636 incorporated herein by reference in its entirety, and subsequently modified by Backes, et al., J. A. J. Org. Chem. 1999, 64, 2322 and Backes, et al., J. Am. Chem. Soc. 1996, 118, 3055, both of which are incorporated herein by reference in their entirety, and then cyclize the linear peptides with concomitant cleavage from the resin—a process known as cleavage-by-cyclization (CBC). The AS-SCL has been used previously for the synthesis of cyclic peptides via CBC, (See Yang, et al., Tetrahedron Lett. 1999, 40, 8197; de Visser, et al., J. Pept. Res. 2003, 61, 298; Qin, et al., J. Comb. Chem. 2003, 5, 353; Bu, et al, J. Org. Chem. 2004, 69, 2681; Qin, et al., Chem. 2004, 6, 398; Qin, et al., Tetrahedron Lett. 2004, 45, 217-220; and Bourel-Bonnet, et al., J. Med. Chem. 2005, 48, 1330, the entirety of each is herein incorporated by reference) and resins functionalized with this linker are commercially available, making it a convenient choice for the present method. One skilled in the art would understand that in addition to the CBC method, other methods, including but not limited to, cleavage of the linear precursor followed by cyclization in solution, are also encompassed. The CBC method however eliminates one synthetic step and avoids the strong acid cleavage that is typically required in Boc SPPS (See Stewart, J. M.; Young, J. D. Solid Phase Peptide Synthesis, $2^{nd}$ ed.; Pierce Chemical: Rockford, Ill., 1984).

Figure 6B:
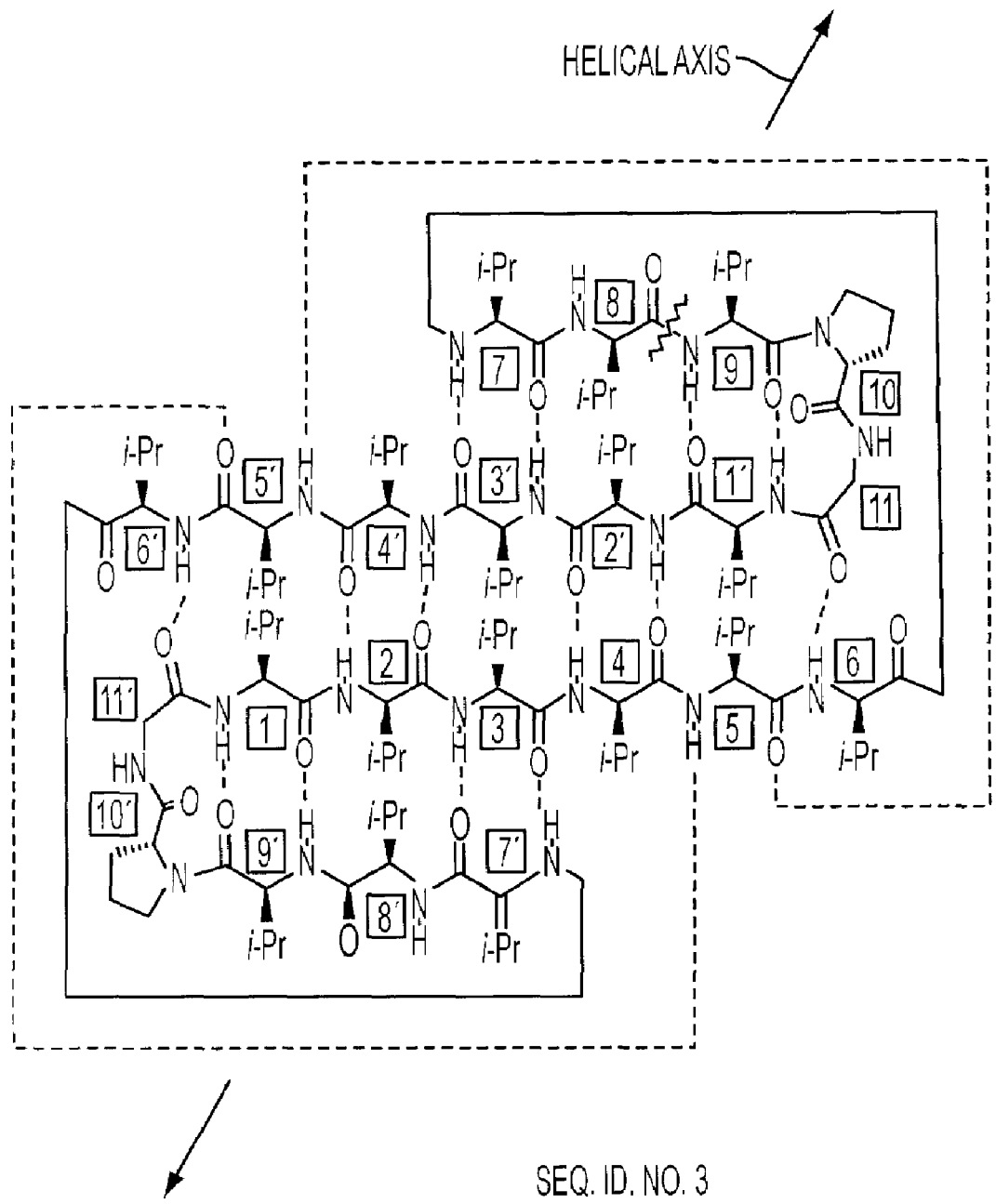
FIG. 6b shows the schematic side view of a $\beta^{5,6}$-helical structure of peptide 3 (SEQ. ID No. 3)

In FIG. 6(*a*), the chemical structures of the peptide 3 (SEQ. ID No. 3) and 4 (SEQ. ID No. 4) are shown: cyclo{[(L-Val-D-Val)$_4$-(L-Val-D-Pro-Gly)]$_2^-$} and cyclo{[(D-Leu-L-Leu)$_4$-(D-Leu-L-Pro-Gly)]$_2^-$}. D residues and Gly are shown in black, while L residues are shown in gray and black; residues that comprise the two symmetry-related halves of the molecules are labeled 1 through 11 and 1' through 11'. The reverse-turn sequences of peptides 3 and 4 (D-Pro-Gly and L-Pro-Gly, respectively) are boxed in gray. In both peptides 3 and 4, the amide bond that is formed during CBC (between the carboxyl of residue 8 and the amine of residue 9) is marked with a wavy line. FIG. 6(b) shows a schematic side view of the $\beta^{5,6}$-helical structure of peptide 3 (SEQ. ID No. 3), showing hydrogen-bonding interactions; peptide 4 (SEQ. ID No. 4) is expected to have an analogous $\beta^{5,6}$-helical structure (not shown). In the linear precursor to 3 (SEQ. ID No. 6), a hydrogen bond between the carboxyl of residue 9 and the NH of residue 10 would position the amino group of residue 9 favorably for amide bond formation with the carboxyl of residue 8.

The target cyclic peptides 3 (SEQ. ID No. 3) and 4 (SEQ. ID No. 4) are both 22 residues long, while those prepared previously via CBC using the AS-SCL are peptides up to 10 residues long. The ease of macrocyclization reactions tends to correlate inversely with the number of atoms in the ring, and thus the prospect of forming the 66-membered rings of peptides 3 and 4 at first appeared daunting. However, the two reverse-turn regions of each peptide, together with alternating chirality of the residues and intramolecular hydrogen bonding, would cause the lin-3 (SEQ ID No. 6) and lin-4 (SEQ ID No. 7) to fold into preorganized $\beta^{5,6}$-helical structures that would place the N and C termini close in space and thus encourage ring closure. In a retrosynthetic sense, a disconnection between the carboxyl function of residue 8 and the amino group of residue 9 was made (FIG. 6), so that the forward reaction (ring closure) would take place between residues at the ends of the putative helices and avoid any steric congestion in the middle. Furthermore, the hydrogen bonding between the carbonyl of residue 9 and the NH of residue 10 (FIG. 6b), together with the presence of the nearby reverse turn residues, would place the amino group of residue 9 in a favorable position for ring closure.

Peptides 3 (SEQ. ID No. 3) and 4 (SEQ. ID No. 4) differ in polarity from those prepared earlier via CBC using AS-SCL. The previously reported cyclic peptides prepared via CBC using AS-SCL all contained at least one polar residue, while Peptides 3 and 4 are comprised of only nonpolar residues. Therefore, Peptides 3 and 4 are expected to be highly hydrophobic. Although the purification of highly hydrophobic peptides is known to be difficult, (See Bollhagen, et al., J. Chromatogr., A 1995, 711, 181; Lew, et al., Anal. Biochem. 1997, 251, 113; and Taneja, et al., J. Chromatogr. 1984, 317, 1) by using high resolution techniques of separation such as RP-HPLC the inventors obtained products pure enough for characterization by high-field NMR.

Figure 7:
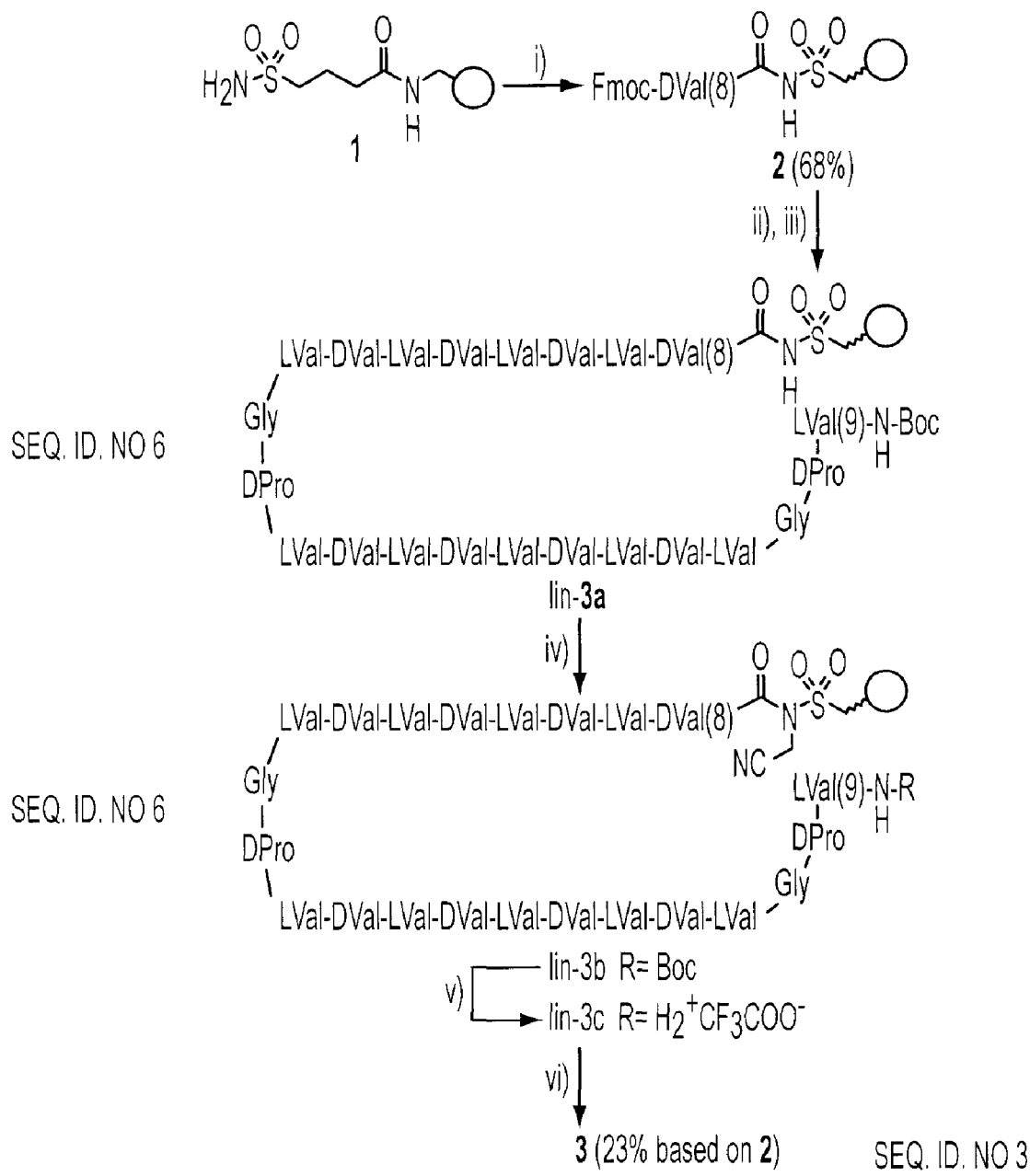
FIG. 7 shows the synthesis scheme of peptide 3.

FIG. 7 shows a schematic of the solid-phase synthesis and purification of Peptide 3: (i) 2× Fmoc-D-Val-F, DIEA, CH$_2$Cl$_2$, room temperature; (ii) 4×20% piperidine in DMF; (iii) Boc SPPS; (iv) ICH$_2$CN, DIEA, NMP; (v) 2×TFA (neat); (vi) DIEA, THF. (In 2 and lin-3a-c (SEQ ID No. 6) the residues that react during ring closure, D-Val(8) and L-Val(9), are numbered as in FIG. 6, while, for clarity, the numbering of all other residues is omitted.)

Discussed is the specific synthesis and purification steps of peptide 3 (SEQ ID No. 3), but the synthesis and purification of peptide 4 (SEQ ID No. 4) and other peptides disclosed herein were carried out in an analogous manner. Beginning with 4-sulfamylbutyryl AM resin 1, anchor the C-terminal residue, D-Val(8), as the preformed Fmoc-amino acid fluoride. The acid fluoride was chosen rather than in situ activation with PyBop for the sake of convenience: the former allowed us to carry out the coupling at room temperature in a SPPS vessel, (see Ingenito et al., Org. Lett. 2002, 4, 1187, incorporated herein in its entirety by reference), while the latter requires the coupling to be carried out at −20° C. in a round-bottom flask. Furthermore, the presence of the Fmoc protecting group allowed for the determination of the yield of the anchoring reaction using the quantitative variant of the Fmoc UV absorbance assay. Here, double coupling with Fmoc-D-Val-F[26] furnished the Fmoc-amino-acylated resin 2 in 68% yield. This modest yield is attributed to the steric hindrance posed by the b-branched side chain of D-Val. Consistent with this interpretation, de Visser et al. reported a yield of 64% for the anchoring of 13-branched Fmoc-L-Thr($^t$Bu)—F to 1, while during the synthesis of peptide 4 (SEQ ID No. 4) the double coupling of the non-β-branched Fmoc-L-Leu-F proceeded in 91% overall yield.

Following the removal of the Fmoc group with 20% piperidine in DMF, the synthesis was continued at the appropriate scale using manual Boc SPPS and following the in situ neutralization protocol of Schnolzer et al., Int. J. Pept. Protein Res. 1992, 40, 180, incorporated herein in its entirety by reference, with the exception that the more efficient coupling reagent HATU was used in place of HBTU, NMP was used in place of DMF, and a combination of flow and shake washes (FSW) was used in place of a single flow wash.

After the final residue, L-Val(9), was coupled, the C terminus of the resin-bound linear peptide lin-3a (SEQ ID No. 6) was activated via cyanomethylation with ICH$_2$CN and DIEA in NMP to give activated species lin-3b (SEQ ID No. 6) The N-terminal Boc group was removed with neat trifluoroacetic acid (TFA) and effected CBC by suspending the TFA-peptidyl resin lin-3c (SEQ ID No. 6) in THF and adding 3 equiv DIEA. The CBC reaction was accompanied by the formation of a white precipitate, which we collected by filtering the resin and washing copiously with CHCl$_3$. Evaporation of the CHCl$_3$ yielded crude peptide 3 (SEQ ID No. 3).

Purification and characterization of peptide 3: Crude peptide 3 (SEQ ID No. 3) proved insoluble in solvents such as MeOH, EtOH, i-PrOH, and CH$_3$CN that are typically used for RP-HPLC; the inventors attribute this insolubility to the highly hydrophobic nature of the peptide. However, dissolution of the crude peptide in HFIP at a concentration of about 80 mg mL$^{-1}$, followed by twofold dilution with HFA.3H$_2$O, furnished a solution that was suitable for use in RP-HPLC. Initial attempts at RP-HPLC using a C4 column with CH$_3$CN/water failed to elute any peaks, but switching to i-PrOH/water and also using a C4 column gave predominantly a single, broad peak (FIG. 8), which were collected as two fractions (fractions a and b) and analyzed using MS and $^1$H NMR spectroscopy. Both RP-HPLC fractions showed the anticipated molecular ions by MALDI-MS. 1D $^1$H NMR spectroscopy revealed that fraction a consisted of about 10:1 ratio of major and minor species (FIG. 9a), which was tentatively assigned as the desired peptide 3 (SEQ ID No. 3) and an epimerized product, respectively; this assignment was supported by the absence of additional peaks in the mass spectrum, which suggests that the minor species has the same molecular weight as the desired peptide 3 (SEQ. ID No. 3). In addition, NMR spectroscopy indicated that fraction b contained the desired peptide 3 (SEQ. ID No. 4), the putative epimerized material, and at least one additional contaminant (FIG. 9b).

Figure 9A:
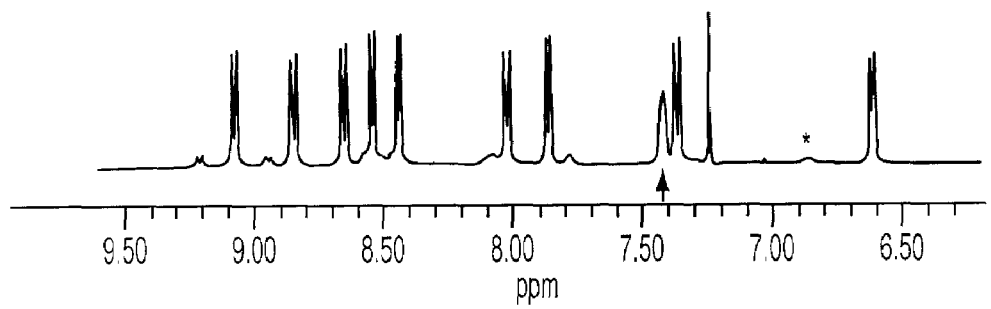
FIG. 9a-d shows the NH region of the 1D $^1$H NMR spectra of peptides 3 and 4.
Figure 9B:
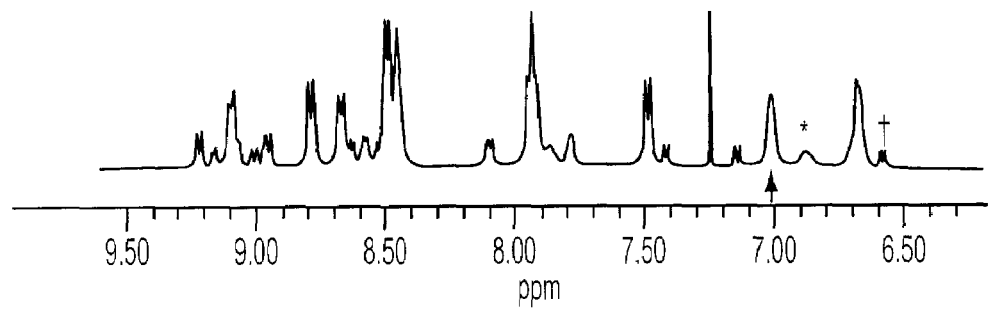

The chemical shifts of the corresponding amide protons in FIGS. 9a and 9b differ somewhat due to differing amounts of water and impurities in the two samples. When the inventors sought to purify both fractions further using RP-HPLC, they found that repeated chromatography on a C4, C8, or C18 column failed to completely remove the putative epimerized material.

Figure 9C:
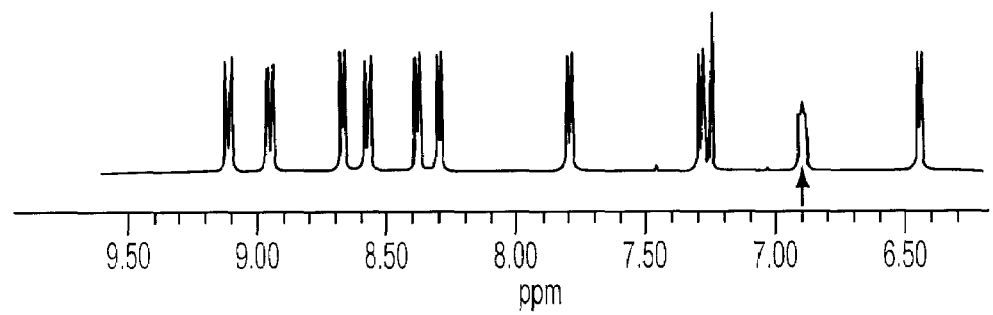
Figure 9D:
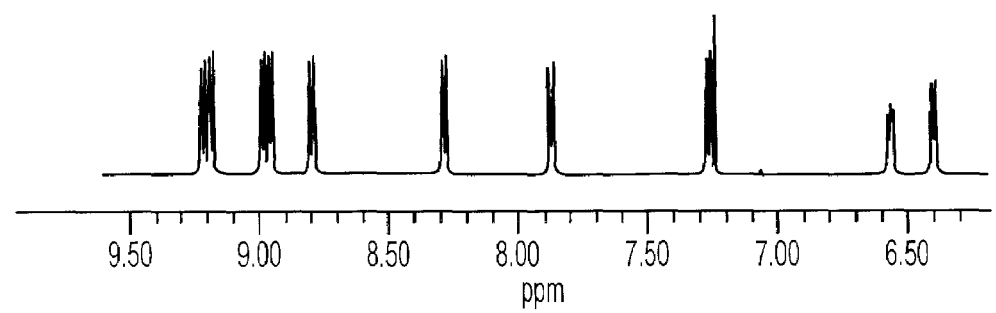

The next attempt to repurify fraction a of the RP-HPLC purified material using gravity-driven GPC on Sephadex LH-20. These efforts were complicated by the lack of a suitable pure solvent that would satisfy the following criteria: (1) the solvent must be able to dissolve the partially purified peptide, and (2) the solvent must be sufficiently polar to prevent irreversible adsorption of the peptide to the LH-20 stationary phase. One choice was $CHCl_3$, in which the peptide is soluble to about. 20 mM; $CHCl_3$, however, is a nonpolar solvent. Moreover, $CHCl_3$ is denser than LH-20 and therefore inconvenient for GPC using gravity-driven flow. However, the solvent mixture $CHCl_3$/MeOH (65:35) satisfies both of the criteria stated above; in addition, this mixture is less dense than LH-20. A single pass of fraction a through a 2.5×55 cm column of LH-20 in $CHCl_3$/MeOH gave material that was ≧95% pure as estimated by 1D $^1H$ NMR (FIG. 9c). Furthermore, even fraction b of the RP-HPLC-purified material, which contained about 30% contaminant (FIG. 9b), could be purified in this manner. Using this two-step method of purification, both peptides 3 and 4 were obtained in about 23% yield based on Fmoc-aminoacyl resin (e.g., 2). FIGS. 9c and 9d, respectively, shows the 1D $^1H$ NMR spectra of peptides 3 (SEQ. ID No. 3) and 4 (SEQ. ID No. 4) after RP-HPLC/GPC purification and thorough drying. Both spectra consist of a single set of sharp, well-dispersed resonances, with no minor peaks that would indicate multiple conformers or oligomers interconverting on the NMR time scale. Three additional observations concerning the NMR spectra support the expected $\beta^{5,6}$-helicalstructures of peptides 3 and 4. First, both the $^1H$ and proton-decoupled $^{13}C$ spectra are consistent with the anticipated two-fold symmetrical structures of the 22-mers: the NH region of each $^1H$ spectrum (FIGS. 9c and 9d, $\delta$ 6.44-9.23) contains the expected 10 NH peaks, while the $^{13}C$ spectra each contain 11 peaks in the carbonyl region (C', $\delta$ 169-175) and 11 peaks in the $C^\alpha$ region ($\delta$ 47-62). Second, both $^1H$ spectra (FIGS. 9c and 9d) show 8 NH resonances downfield from 7.2 ppm, chemical shifts consistent with the 16 hydrogen bonds anticipated for the $\beta^{5,6}$-helical structures of peptides 3 and 4. Finally, the majority of the $^3J_{NH-H\alpha}$ values in the $^1H$ spectra are greater than 8 Hz, which is typical for residues having $\beta$-sheet-like $\phi$ dihedral angles. The detailed structural analysis of peptides 3 and 4 using 2D $^1H$ NMR spectroscopy and structure calculations is reported elsewhere.

Additional experimental details: Before use, DIEA was distilled first from ninhydrin and then from $CaH_2$, and $CH_2CN$ was filtered through a plug of basic alumina; otherwise, all materials were used as received from the source indicated: 4-sulfamylbutyryl AM resin, EMD Biosciences, San Diego, Calif., USA; anhydrous $CH_2Cl_2$ and THF, Sigma-Aldrich, Milwaukee, Wis., USA; anhydrous NMP (Biotech Grade, over 4 Å molecular sieves), Pharmco, Brookfield, Conn., USA; HATU, Applied Biosystems, Foster City, Calif., USA; HFIP, TCI America, Portland, Oreg., USA; HFA$3H_2O$, Sigma-Aldrich; and Sephadex LH-20, Amersham Biosciences, Piscataway, N.J., USA. $CHCl_3$ used in GPC was of HPLC-grade and stabilized with about 50 ppm pentene.

General procedures for manual solid-phase peptide synthesis. Procedure for flow/shake washes (FSW) A single round of FSW consisted of a brief (about 10-15 s) vacuum-assisted flow wash (about. 5 mL $s^{-1}$), taking care not to let the resin go dry, followed by a 5 s shake with about 10 mL solvent.

Representative procedures for manual solid-phase peptide synthesis. Synthesis of peptide 3 (SEQ. ID No. 3) cyclo{[(L-Val-D-Val)$_4$-(L-Val-D-Pro-Gly)]$_2^-$}: Anchoring the first amino acid: 4-Sulfamylbutyryl AM resin (1.0 mmol, 0.91 g of 1.1 mequiv $g^{-1}$, 1 equiv) was placed in a SPPS vessel having a coarse porosity sintered glass frit and Teflon stopcock. Anhydrous $CH_2Cl_2$ (10 mL) was added and the resin was allowed to swell by shaking for 1 h. The $CH_2Cl_2$ was drained to the top of the resin, taking care not to let the resin go dry, and the resin was rinsed using two rounds of FSW. A solution of Fmoc-D-Val-F$^{26}$ (1.02 g, 3 mmol, 3 equiv) in anhydrous $CH_2Cl_2$ (6 mL) was added, followed by DIEA (0.35 mL, 2 mmol, 2 equiv), and the reaction mixture was shaken for 1 h and then drained. After 2×FSW with $CH_2Cl_2$, the coupling was repeated as before. The resin was again rinsed via 2×FSW with $CH_2Cl_2$, followed by $Et_2O$, and then dried overnight under vacuum. Two ca. 5 mg samples of the aminoacyl resin were removed and subjected to the quantitative Fmoc UV absorbance assay, by which the loading of the resin was determined to be 0.60 mmol $g^{-1}$ (coupling yield was about 68%). A portion of the resin (600 mg) was removed and transferred to another SPPS vessel, and the synthesis was carried forward at the appropriate scale (0.36 mmol).

Elongation of the peptide chain. The Fmoc group of the aminoacyl resin obtained by using the procedure above was removed by shaking with 20% piperidine in DMF for 4×3 min and the resin was rinsed via 2×FSW with NMP. The synthesis was then carried forward using Boc manual SPPS according to the following modified version of the in situ neutralization protocol: Boc-amino acid (1.44 mmol, 4 equiv) and HATU (0.521 g, 1.37 mmol, 3.8 equiv) were dissolved in anhydrous NMP (3 mL) and DIEA was added (0.38 mL, 2.16 mmol, 6 equiv). The mixture was shaken until a homogeneous solution was obtained and then allowed to sit for an additional 1 min in order to preactivate the amino acid. The resulting solution of activated amino acid was added to the peptidyl resin; the resin was shaken for 30 min and then rinsed via 2×FSW with NMP. The resin was tested for the presence of unreacted amines using the qualitative ninhydrin test (for primary amines) or the qualitative chloranil test (for secondary amines), and couplings that yielded a positive test were repeated. If the resin continued to give a positive test after recoupling, it was capped by treatment with $Ac_2O$ (0.34 mL, 3.6 mmol, 10 equiv) and DIEA (0.31 mL, 1.8 mmol, 5 equiv) in NMP (5 mL) for 2 h. When all the amino groups had reacted, the N-terminal Boc group was deprotected by shaking for 2×1 min with neat TFA and the resin was rinsed via 3×FSW with NMP. The next Boc-amino acid was then coupled as before.

Activation and cyclization. When the last Boc-amino acid had been coupled, the N-terminal Boc group was left on, and the C terminus was activated by shaking the resin for 24 h with $ICH_2CN$ (0.66 mL, 9.08 mmol, 25 equiv) and DIEA (0.63 mL, 3.63 mmol, 10 equiv) in NMP (5 mL). The resin was rinsed via 3×FSW with NMP, the N-terminal Boc group was removed as before, and the resin was washed via 3×FSW with NMP and 3×FSW with anhydrous THF. The resin was then transferred to a round-bottom flask; anhydrous THF (7 mL) was added, followed by DIEA (127 mL, 1.09 mmol, 3 equiv), and the resulting reaction mixture was stirred magnetically under Ar. Although a white precipitate began to form within 1 h, the mixture was stirred for 3 days in order to ensure complete reaction. The crude peptide 3 (SEQ ID No. 3) was collected by filtering the resin through a medium porosity sintered glass funnel and rinsing copiously with $CHCl_3$ (about 100 mL). Removal of the $CHCl_3$ under reduced pressured afforded crude peptide 3 (431 mg).

Representative procedure for RP-HPLC. Chromatography of crude peptide 3: Crude peptide 3 (SEQ. ID No. 3) (431 mg) was dissolved in HFIP (about 5 mL) and diluted with HFA.3$H_2O$ (about 10 mL). The resulting solution was clarified by filtration using a 0.45-mm in-line syringe filter, and then subjected to RP-HPLC in 3 mL injections on a 22×250 mm C4 column run at 20 mL min$^{-1}$ using a gradient of 60%

Figure 8:
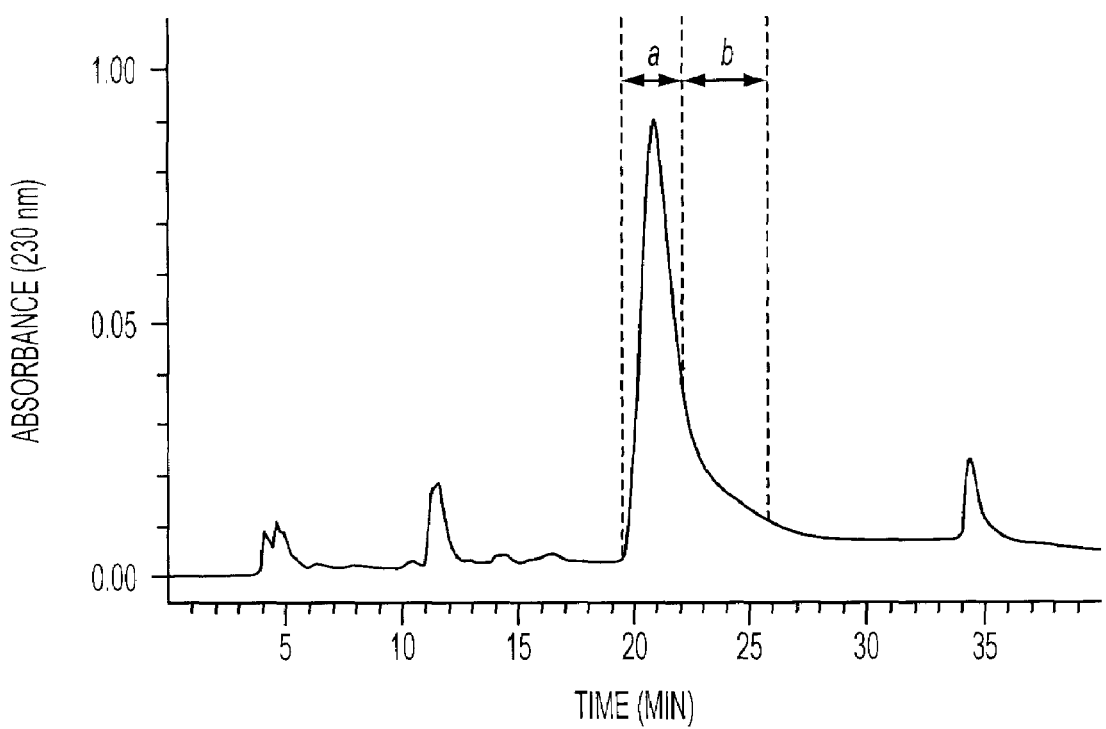
FIG. 8 is the RP-HPLC profile of as-synthesized crude peptide 3.

B to 77% B over 17 min (solvent A is 0.1% TFA and 1% i-PrOH in H$_2$O; solvent B B is 0.07% TFA and 90% i-PrOH in H$_2$O). The absorbance of the eluant was monitored at 230 nm, and the major peak was collected as two fractions as indicated in FIG. 8. Yield: fraction a, 145 mg; fraction b, 73 mg.

Chromatography of HPLC-purified peptide 3 (SEQ ID No. 3); Fraction a of RP-HPLC-purified peptide 3 (140 mg) was dissolved in 10 mL CHCl$_3$/MeOH (65:35 v/v), and 5 mL of this solution was loaded onto a 2.5×55 cm column of LH-20 in CHCl$_3$/MeOH (65:35 v/v; degassed separately before mixing) using a Pasteur pipette, taking care not to let the top of the resin go dry. The column was then run overnight using gravity-driven flow at about 1 mL min$^{-1}$. Fractions of 5 mL were collected, and peptide-containing fractions were identified by transferring an aliquot to a quartz cuvette and reading the absorbance at 245 nm. Pure peptide 3 (SEQ. ID No. 3) eluted first, followed by the putative epimerized material, and the two species were typically separated by 2-3 fractions that contained no peptide. The remaining 5 mL of fraction a was chromatographed in an identical manner. Fraction b of the HPLC-purified material was dissolved in 5 mL CHCl$_3$/MeOH 65:35 v/v and chromatographed in a single aliquot as described above. In this manner, a total of 170 mg of pure 3 (SEQ ID No. 3) was obtained (0.083 mmol, 23% based on 2).

For the synthesis of peptide 4, (SEQ ID No. 4) resin 1 (0.45 g, 0.5 mmol, 1 equiv) was loaded with Fmoc-L-Leu-F$^{26}$ (0.53 g, 1.5 mmol, 3 equiv) in 91% yield as described above for peptide 3. The remainder of the synthesis and purification of peptide 4 was then carried out analogously to the procedures used for peptide 3, to give 245 mg pure peptide 4 (0.104 mmol, 23% yield).

Spectral characterization of peptides 3 and 4: Mass spectral analysis was performed by the Laboratory for Biological Mass Spectrometry of Texas A&M University (College Station, Tex., USA). Samples of RP-HPLC/GPC purified peptides 3 and 4 were dried under vacuum for at least 12 h prior to NMR analysis. $^1$H NMR and proton-decoupled $^{13}$C NMR spectra were referenced to CHCl$_3$ (7.24 ppm) and CDCl$_3$ (77.0 ppm), respectively. The $^1$H NMR resonances were assigned using 2D NMR spectroscopy. The $^{13}$C NMR resonances were partially assign by comparison of the 1D proton-decoupled $^{13}$C spectra with residue-dependent chemical shift values from the literature, and by cross-correlating the shifts observed for peptides 3 and 4. No attempt was made to more fully assign the $^{13}$C resonances. Due to the twofold symmetry of peptides 3 and 4, NMR signals were observed corresponding to only half the total number of residues. IR spectra were recorded on a Nicolet 750 FTIR spectrometer at a resolution of 8 cm$^{-1}$, and samples were held in a liquid cell having BaF$_2$ windows and a path length of 50 μm. IR spectra were corrected for background by taking the ratio of the sample spectra to a blank spectrum.

Peptide 3 (SEQ ID No. 3) cyclo{[(L-Val-D-Val)$_4$-(L-Val-D-Pro-Gly)]$_2$—}. $^1$H NMR (500 MHz, 289 K, 10 mM in CDCl$_3$): L-Val(1), NH (7.28, d, J=9.6 Hz), C$^\alpha$H (4.74), C$^\beta$H (2.12), C$^\gamma$H$_3$ (0.95, 0.91); D-Val(2), NH (8.68, d, J=6.3 Hz), C$^\alpha$H (4.64), C$^\beta$H (2.32), C$^\gamma$H$_3$ (1.03, 0.99); L-Val(3), NH (8.58, d, J=9.8 Hz), C$^\alpha$H (4.89), C$^\beta$H (2.00), C$^\gamma$H$_3$ (0.92, 0.84); D-Val(4), NH (8.38, d, J=6.8 Hz), C$^\alpha$H (4.76), C$^\beta$H (2.10), C$^\gamma$H$_3$ (0.95); L-Val(5), NH (8.96, d, J=10.1 Hz), C$^\alpha$H (5.11), C$^\beta$H (2.06), C$^\gamma$H$_3$ (0.90, 0.81); D-Val(6), NH (8.30, d, J=7.5 Hz), C$^\alpha$H (4.62), C$^\beta$H (2.10), C$^\gamma$H$_3$ (0.94, 0.90); L-Val (7), NH (9.14, d, J=9.1 Hz), C$^\alpha$H (4.03), C$^\beta$H (1.91), C$^\gamma$H$_3$ (0.89); D-Val(8), NH (6.45, d, J=6.4 Hz), C$^\alpha$H (4.92), C$^\beta$H (2.20), C$^\gamma$H$_3$ (1.06, 0.93); L-Val(9), NH (7.78, d, J=8.4 Hz), C$^\alpha$H (4.39), C$^\beta$H (2.13), C$^\gamma$H$_3$ (1.05, 0.95); D-Pro(10), C$^\alpha$H (4.40), C$^\beta$H (2.27, 2.05), C$^\gamma$H$_3$ (2.02), CdH (4.27, 3.63); Gly (11), NH (6.91), C$^\alpha$H (4.31, 3.60). $^{13}$C NMR (75 MHz, 295 K, 10 mM in CDCl$_3$): δ 173.2 (C'), 172.5 (C'), 172.1 (C'), 171.8 (C'), 171.7 (C'), 171.4 (C'), 171.3 (C'), 171.2 (C'), 170.8 (C'), 170.7 (C'), 169.5 (C'), 61.7 (D-Pro10 C$^\alpha$), 59.0 (Val C$^\alpha$), 59.0 (Val C$^\alpha$), 58.9 (Val C$^\alpha$), 58.8 (Val C$^\alpha$), 58.6 (Val C$^\alpha$), 58.0 (Val C$^\alpha$), 57.2 (Val C$^\alpha$), 56.6 (Val C$^\alpha$), 56.2 (Val C$^\alpha$), 48.0, 42.5, 32.4, 32.4, 32.2, 31.7, 31.7, 31.6, 31.3, 30.6, 30.5, 29.6, 25.9 (D-Pro10 C$^\gamma$), 20.1 (Val C$^\gamma$), 19.9 (Val C$^\gamma$), 19.8 (Val C$^\gamma$), 19.7 (Val C$^\gamma$), 19.6 (Val C$^\gamma$), 19.5 (Val C$^\gamma$), 19.4 (Val C$^\gamma$), 19.3 (Val C$^\gamma$), 19.3 (Val C$^\gamma$), 19.3 (Val C$^\gamma$), 19.2 (Val C$^\gamma$), 19.0 (Val C$^\gamma$), 18.9 (Val C$^\gamma$), 18.7 (Val C$^\gamma$), 18.4 (Val C$^\gamma$), 17.8 (Val C$^\gamma$), 17.7 (Val C$^\gamma$), 17.2 (Val C$^\gamma$) ppm. IR (liquid, BaF$_2$, 295 K, 2 mM in CDCl$_3$): v 3413 (amide A, nonhydrogen-bonded), 3278 (amide A, hydrogen-bonded), 3066 (amide B), 1682 (amide I parallel component), 1635 (amide I perpendicular component), 1543 (amide II) cm$^{-1}$. HRMS (MALDI) m/z calcd for C$_{104}$H$_{183}$N$_{22}$O$_{22}$ [M+H]$^+$: 2092.3877. found: 2092.3845; calcd for C$_{104}$H$_{182}$N$_{22}$NaO$_{22}$ [M+Na]$^+$: 2114.3697. found: 2114.3662; calcd for C$_{104}$H$_{182}$N$_{22}$KO$^{22}$ [M+K]$^+$: 2130.3436. found: 2130.3501.

Peptide 4 (SEQ ID No. 4) cyclo{[(D-Leu-L-Leu)$_4$-(D-Leu-L-Pro-Gly)]$_2$-}. $^1$H NMR (600 MHz, 283 K, 12 mM in CDCl$_3$): D-Leu(1), NH (7.28, d, J=8.9 Hz), C$^\alpha$H (4.75), C$^\beta$H (1.64, 1.54), C$^\delta$H$_3$ (0.86, 0.80); L-Leu(2), NH (8.92, d, J=7.1 Hz), C$^\alpha$H (4.62), C$^\beta$H (1.77, 1.37), C$^\gamma$H (1.48), C$^\delta$H$_3$ (0.93, 0.87); D-Leu(3), NH (8.80, d, J¼9.3 Hz), C$^\alpha$H (4.81), C$^\beta$H (1.54, 1.42); L-Leu(4), NH (8.35, d, J=8.4 Hz), C$^\alpha$H (4.79), C$^\beta$H (1.59, 1.14), C$^\alpha$H (1.37), C$^\beta$H$_3$ (0.81, 0.82); D-Leu(5), NH (9.22, d, J=9.4 Hz), C$^\alpha$H (4.85), C$^\beta$H (1.62, 1.35), C$^\delta$H$_3$ (0.86, 0.79); L-Leu(6), NH (8.95, d, J=8.3 Hz), C$^\alpha$H (4.67), C$^\beta$H (1.71, 1.32), C$^\alpha$H (1.43), C$^\delta$H$_3$ (0.87); D-Leu(7), NH (9.23, d, J=9.0 Hz), C$^\alpha$H (4.32), C$^\beta$H (1.61, 1.37), C$^\gamma$H (1.58), C$^\delta$H$_3$ (0.87); L-Leu(8), NH (6.44, d, J=6.9 Hz), C$^\alpha$H (4.99), C$^\beta$H (1.59, 1.48), C$^\delta$H$_3$ (0.94); D-Leu(9), NH (7.85, d, J=7.7 Hz), C$^\alpha$H (4.60), C$^\beta$H (1.71), C$^\gamma$H (1.63), C$^\delta$H$_3$ (0.98, 0.94); L-Pro(10), C$^\alpha$H (4.40), C$^\beta$H (2.28, 2.03), C$^\gamma$H (2.06), C$^\delta$H (4.74, 3.60); Gly(11), NH (6.70, dd, J=4.8, 7.9 Hz), C$^\alpha$H (4.22, 3.44). $^{13}$C NMR (75 MHz, 295 K, 12 mM in CDCl$_3$): δ 174.7 (C'), 173.2 (C'), 172.5 (C'), 172.2 (C'), 171.5 (C'), 171.4 (C'), 171.4 (C'), 171.2 (C'), 170.7 (C'), 170.6 (C'), 169.8 (C'), 61.8 (1-Pro10 Ca), 51.9 (Leu Ca), 51.9 (Leu Ca), 51.3 (Leu C$^\alpha$), 51.1 (Leu C$^\alpha$), 51.0 (Leu C$^\alpha$), 51.0 (Leu C$^\alpha$), 50.9 (Leu C$^\alpha$), 50.8 (Leu C$^\alpha$), 50.1 (Leu C$^\alpha$), 47.7, 43.8, 43.3, 43.1, 42.6, 42.4, 42.3, 42.0, 41.6, 41.0, 40.2, 29.4, 25.2, 25.1, 25.0, 25.0, 24.9, 24.8, 24.8, 24.7, 24.6, 24.5, 23.7 (Leu C$^\delta$), 23.6 (Leu C$^\delta$), 23.3 (Leu C$^\delta$), 23.2 (Leu C$^\delta$), 23.2 (Leu C$^\delta$), 23.0 (Leu C$^\delta$), 22.9 (Leu C$^\delta$), 22.8 (Leu C$^\delta$), 22.7 (Leu C$^\delta$), 22.7 (Leu C$^\delta$), 22.7 (Leu C$^\delta$), 22.4 (Leu C$^\delta$), 22.4 (Leu C$^\delta$), 22.3 (Leu C$^\delta$), 22.2 (Leu C$^\delta$), 21.8 (Leu C$^\delta$), 21.7 (Leu C$^\delta$), 21.7 (Leu C$^\delta$) ppm. IR (liquid, BaF$_2$, 295 K, 2 mM in CDCl$_3$): v 3417 (amide A, nonhydrogen-bonded), 3267 (amide A, hydrogen-bonded), 3070 (amide B), 1682 (amide I parallel component), 1639 (amide I perpendicular component), 1551 (amide II) cm$^{-1}$. HRMS (MALDI) m/z calcd for C$_{122}$H$_{219}$N$_{22}$O$_{22}$ [M+H]$^+$: 2344.6694. found: 2344.6670; calcd for C$_{122}$H$_{218}$N$_{22}$NaO$_{22}$ [M+Na]$^+$: 2366.6514. found: 2366.6489; calcd for C$_{122}$H$_{218}$N$_{22}$KO$_{22}$ [M+K]$^+$: 2382.6253. found: 2382.6099.

Figure 10A:
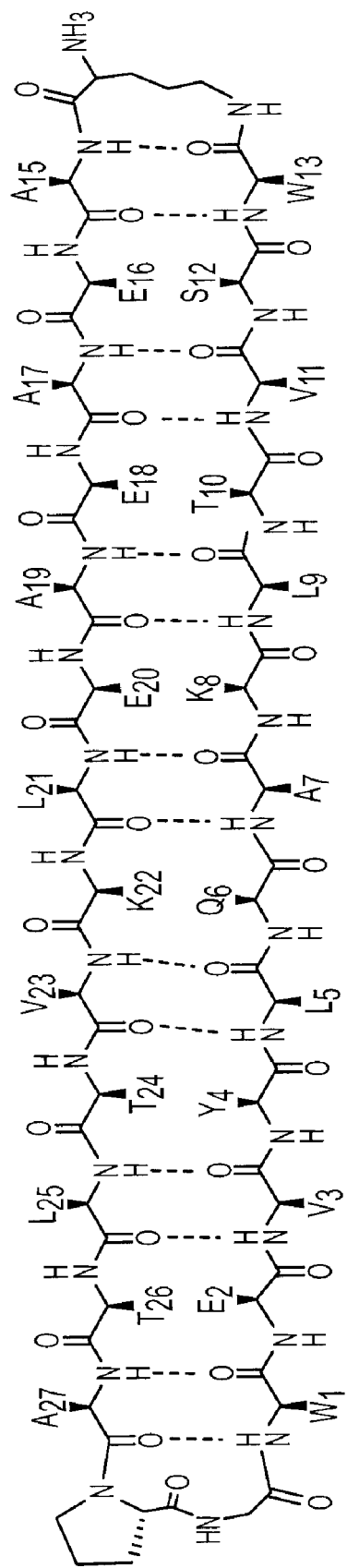
FIG. 10a shows the primary sequence of peptide 2 (SEQ. ID No. 2)
Figure 10B:
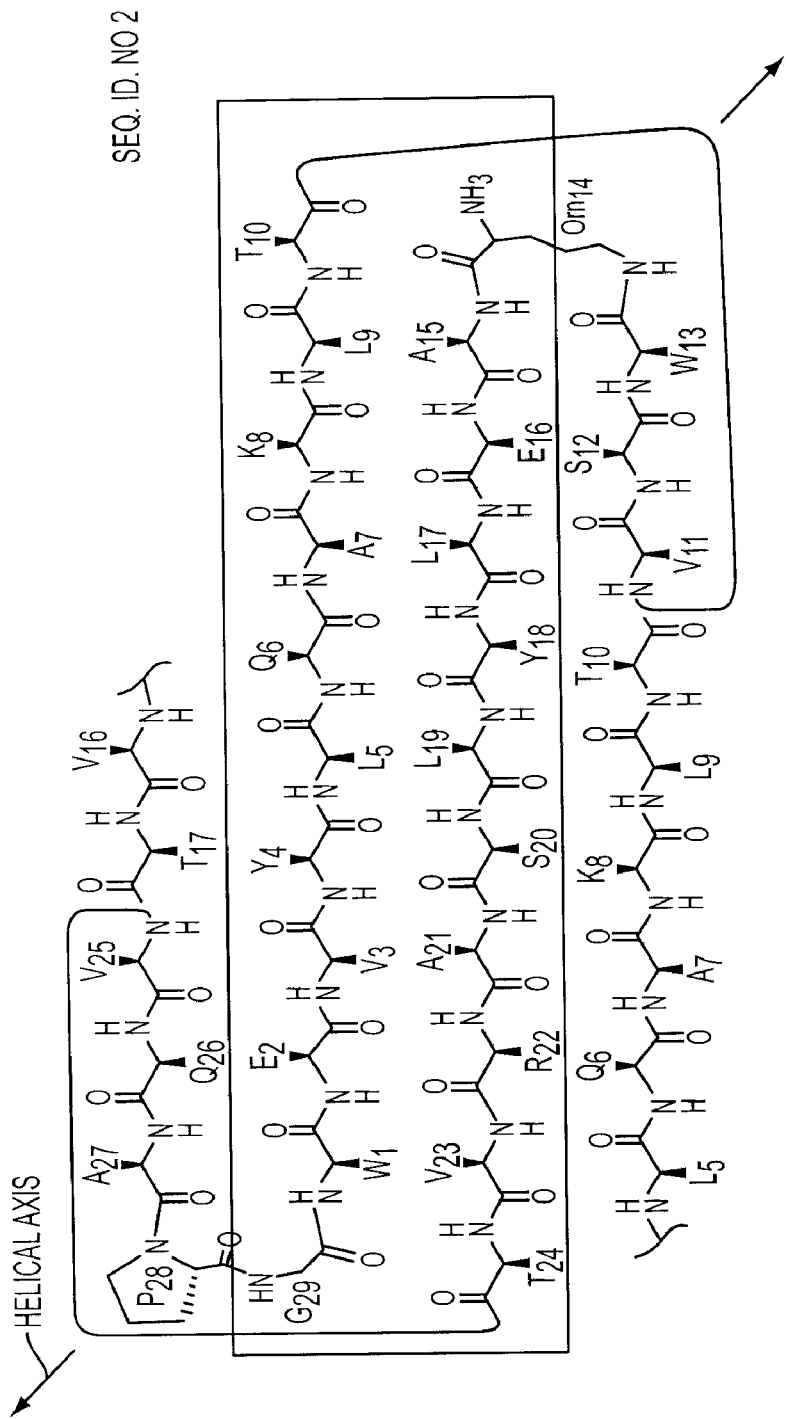
FIG. 10b shows a schematic view of a $\beta^{5,6}$-helical structure of peptide 2 (SEQ. ID No. 2)

Additionally, other stabilized peptide structures have been synthesized using the disclosed methods. Further, the method disclosed herein takes into account that increasing the length of the peptide strands will increase the number of helical hydrogen bonds, which should increase the overall stability of the helical fold. FIG. 10a shows peptide 2 (SEQ ID No. 2) which is comprised of two 13-residue segments which contain alternating D,L-β-amino acids (residues 1-13 and 15-27, FIG. 10a). This increased length yields four additional helical hydrogen bonds in a β$^{5.6}$ helix (FIG. 10b). The two D,L-peptide strands were joined using two 13-turn sequences, L-Pro-Gly and L-Orn. FIG. 10a shows the primary sequence for peptide 2 (SEQ ID No. 2), showing the β-strand and β-turn design; L residues are in gray, while D residues and glycines are in black. FIG. 10b shows the primary sequence for peptide 2 (SEQ ID No. 2), the box highlights the β-helical design, with the superstrand.

Figure 11:
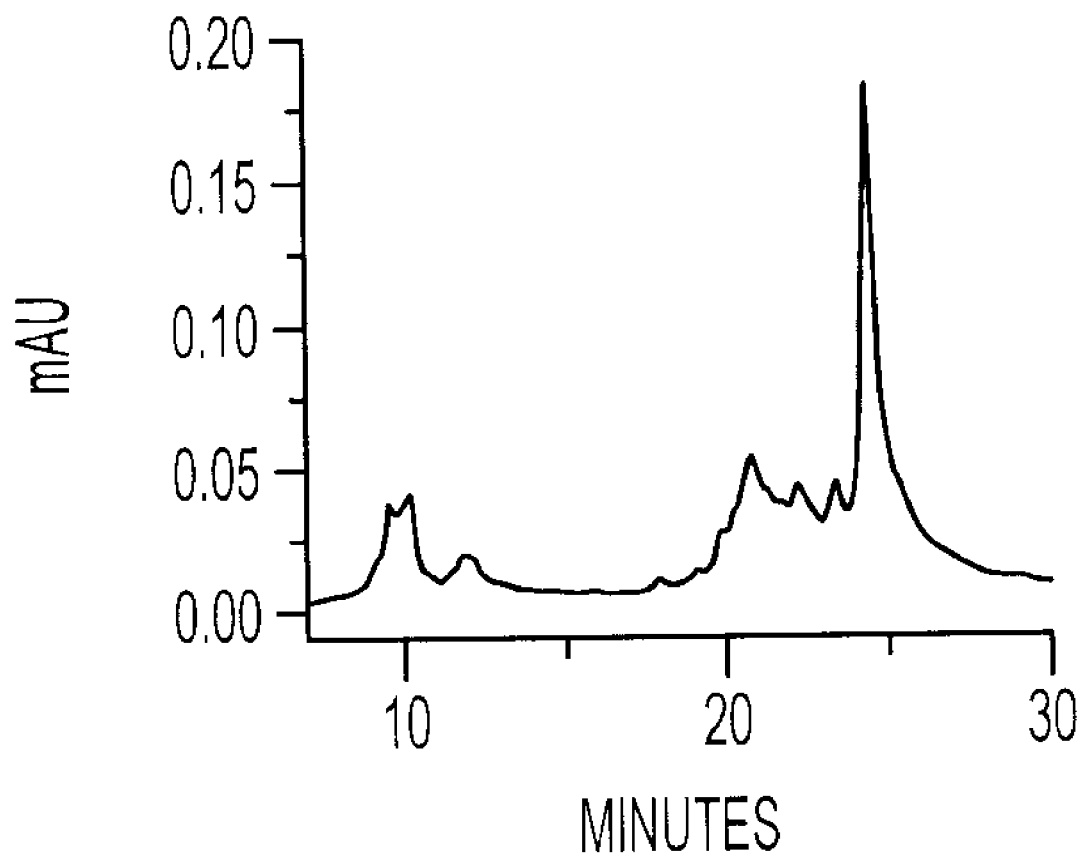
FIG. 11 is a chart of the crude HPLC trace for peptide 2.
Figure 12A:
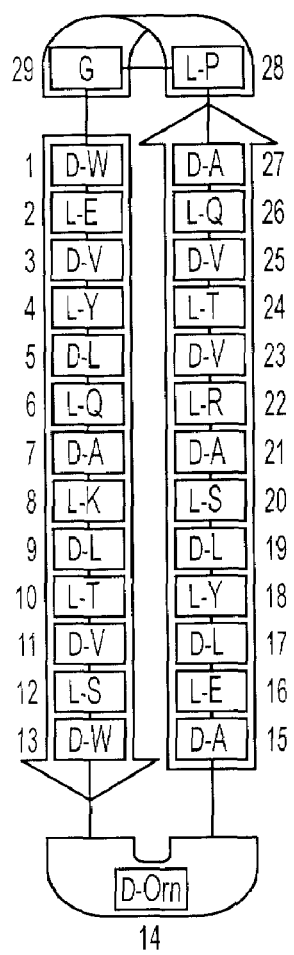
FIG. 12a shows the primary sequence for peptide 2 (SEQ. ID No. 2)
Figure 12B:
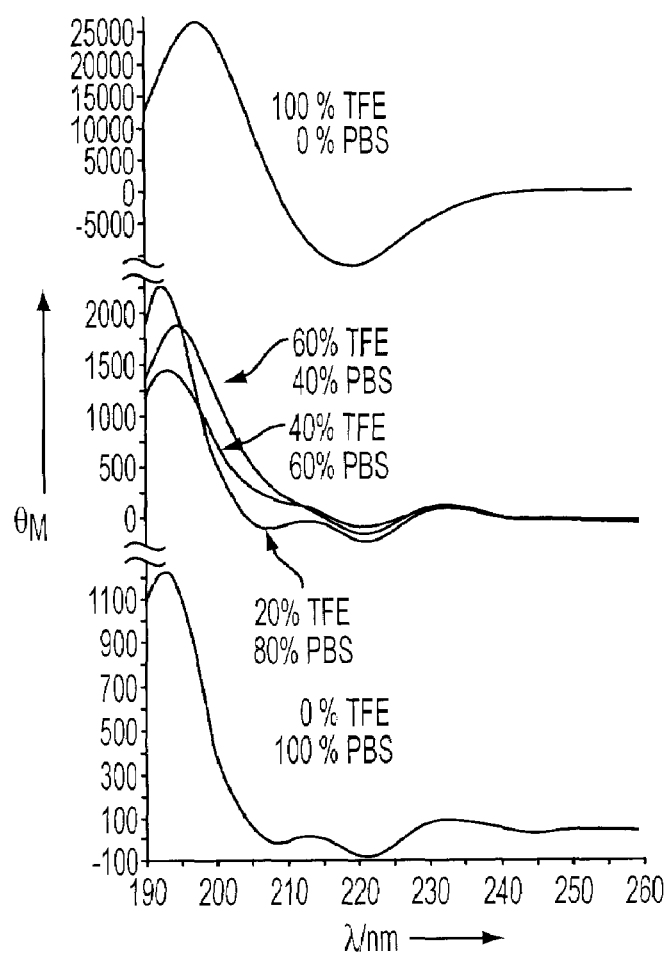
FIG. 12b shows the Far-UV CD spectra for peptide 2.

The far-UV CD spectrum of peptide 2 (SEQ ID No. 2) in TFE shows a spectrum attributed to a left-hand β-hairpin/β[5,6] helical structure (FIG. 12b). During the titration of 1.0 mM PBS, the helical band at 220 nm remains while a new band at 206 nm appears. The data confirms that the majority population in an aqueous environment is in a β-helical conformation. FIG. 11 shows the crude HPLC trace for peptide 2 (SEQ ID No. 2). The major peak is desired product.

FIG. 12a shows the primary sequence for peptide 2 (SEQ ID No. 2), showing the β-strand and β-turn design; L residues are boxed in grey, while D residues and glycines are boxed in black. The block arrows indicate roles as β strands in the expected β-hairpin/β-helical structure. FIG. 12b shows the far-UV CD spectra of peptide 2 in TFE (295 K, c=0.02 mM, l=0.1 cm) containing varying volume percentages of phosphate-buffered saline (PBS, 1 mM, pH=7). $\theta_M$=(mean molar ellipticity per residue)÷$10^4$.

The sequences for other peptides that have been synthesize to date by this method include: Peptide 5 (SEQ ID No. 5): 16 amino acids, linear D-Val, (2) L-Val, (3) D-Val, (4) L-Val, (5) D-Val, (6) L-Val, (7) D-Val, (8) L-Val, (9) D-Val, (10) L-Pro, (11) Gly, (12) D-Val, (13) L-Val, (14) D-Val, (15) L-Val, (16) D-Val.

```
Peptide 1 (SEQ ID No. 1): 22 amino acids, cyclic:
  (1) D-Leu,
  (2) L-Glu,
  (3) D-Val,
  (4) L-Arg,
  (5) D-Leu,
  (6) L-Thr,
  (7) D-Ala,
  (8) L-Thr,
  (9) D-Val,
 (10) L-Pro,
 (12) D-Ala,
 (13) L-Glu,
 (14) D-Leu,
 (15) L-Lys,
 (16) D-Val,
 (17) L-Thr,
 (18) D-Leu,
 (19) L-Thr,
 (20) D-Ala,
 (21) L-Pro,
 (22) Gly
```

```
Peptide 2 (SEQ ID No. 2): 29 amino acids, cyclic:
  (1) D-Trp,
  (2) L-Glu,
  (3) D-Val,
  (4) L-Tyr,
  (5) D-Leu,
  (6) L-Gln,
  (7) D-Ala,
  (8) L-Lys,
  (9) L-Leu,
 (10) L-Thr,
 (11) D-Val,
 (12) L-Ser,
 (13) D-Trp,
 (14) D-Orn,
 (15) D-Ala,
 (16) L-Glu,
 (17) D-Leu,
 (18) L-Tyr,
 (19) D-Leu,
 (20) L-Ser,
 (21) D-Ala,
 (22) L-Arg,
 (23) D-Val,
 (24) L-Thr,
 (25) D-Val,
 (26) L-Gln,
 (27) D-Ala,
 (28) L-Pro,
 (29) Gly
```

```
Peptide 3 (SEQ ID No. 3): 22 amino acids, cyclic
  (1) L-Val,
  (2) D-Pro,
  (3) Gly,
  (4) L-Val,
  (5) D-Val,
  (6) L-Val,
  (7) D-Val,
  (8) L-Val,
  (9) D-Val,
 (10) L-Val,
```

(11) D-Val,

(12) L-Val,

(13) D-Pro,

(14) Gly,

(15) L-Val,

(16) D-Val,

(17) L-Val,

(18) D-Val,

(19) L-Val,

(20) D-Val,

(21) L-Val,

(22) D-Val

Peptide 4 (SEQ ID No. 4): 22 amino acids, cyclic
(1) D-Leu, (2) L-Pro, (3) Gly, (4) D-Leu, (5) L-Leu, (6) D-Leu, (7) L-Leu, (8) D-Leu, (9) L-Leu,

(10) D-Leu,

(11) L-Leu,

(12) D-Leu,

(13) L-Pro,

(14) Gly,

(15) D-Leu,

(16) L-Leu,

(17) D-Leu,

(18) L-Leu,

(19) D-Leu,

(20) L-Leu,

(21) D-Leu,

(22) L-Leu

Peptide 5 (SEQ ID No. 5): 22 amino acids, linear
(1) D-Val, (2) L-Val, (3) D-Val, (4) L-Val, (5) D-Val, (6) L-Val, (7) D-Val, (8) L-Val, (9) D-Val,

(10) L-Pro,

(11) Gly,

(12) D-Val,

(13) L-Val,

(14) D-Val,

(15) L-Val,

(16) D-Val

Peptide 6 (SEQ ID No. 6): 22 amino acids, linear
(1) L-Val, (2) D-Pro, (3) Gly, (4) L-Val, (5) D-Val, (6) L-Val, (7) D-Val, (8) L-Val, (9) D-Val,

(10) L-Val,

(11) D-Val,

(12) L-Val,

(13) D-Pro,

(14) Gly,

(15) L-Val,

(16) D-Val,

(17) L-Val,

(18) D-Val,

(19) L-Val,

(20) D-Val,

(21) L-Val,

(22) D-Val

Peptide 7 (SEQ ID No. 7): 22 amino acids, linear
(1) D-Leu, (2) L-Pro, (3) Gly, (4) D-Leu, (5) L-Leu, (6) D-Leu, (7) L-Leu, -continued (8) D-Leu,
(9) L-Leu,
(10) D-Leu,
(11) L-Leu,
(12) D-Leu,
(13) L-Pro,
(14) Gly,
(15) D-Leu, -continued

(16) L-Leu,
(17) D-Leu,
(18) L-Leu,
(19) D-Leu,
(20) L-Leu,
(21) D-Leu,
(22) L-Leu

What is claimed is:

1. A method of making a peptide structure that is stable in aqueous and non-aqueous media comprising:

synthesizing a first linear peptide chain comprising alternating D,L- or L,D-amino acids, said first linear peptide chain having an N and C termini;

synthesizing a second linear peptide chain comprising alternating D,L- or L,D-amino acids, said second linear peptide chain having an N and C termini; and joining said first linear peptide chain with said second linear peptide chain with at least one turn region to form a peptide structure, wherein said peptide structure is stable in aqueous and non-aqueous media, and wherein said peptide structure comprises SEQ ID No: 1 or SEQ ID No: 2.

2. The method of claim 1 wherein said joining step comprises joining a C terminus of one of the linear peptide chains with an N terminus of the other linear peptide chain.

3. The method of claim 1 wherein said joining step comprises joining a C terminus of one of the linear peptide chains with a C terminus of the other linear peptide chain.

4. The method of claim 1 wherein said joining step comprises joining an N terminus of one of the linear peptide chains with an N terminus of the other linear peptide chain.

5. The method of claim 1 further comprising purifying said stabilized peptide structure.

6. The method of claim 1, wherein said peptide structure comprises SEQ ID No: 1.

7. The method of claim 1, wherein said peptide structure comprises SEQ ID No: 2.

* * * * *